United States Patent
Rimsa et al.

(10) Patent No.: US 12,279,792 B2
(45) Date of Patent: Apr. 22, 2025

(54) TROCAR POSITIONING APPARATUS AND METHODS FOR USE

(71) Applicant: Tautona Group IP Holding Company, LLC, Redwood City, CA (US)

(72) Inventors: Joseph Rimsa, Palo Alto, CA (US); Geoffrey C. Gurtner, Portola Valley, CA (US)

(73) Assignee: Tautona Group IP Holding Company, LLC, Redwood City, CA (US)

( * ) Notice: Subject to any disclaimer, the term of this patent is extended or adjusted under 35 U.S.C. 154(b) by 0 days.

(21) Appl. No.: 18/525,383

(22) Filed: Nov. 30, 2023

(65) Prior Publication Data
US 2024/0090921 A1   Mar. 21, 2024

Related U.S. Application Data

(62) Division of application No. 16/993,779, filed on Aug. 14, 2020, now Pat. No. 11,871,961.

(60) Provisional application No. 62/948,050, filed on Dec. 13, 2019.

(51) Int. Cl.
*A61B 17/34* (2006.01)
*A61B 17/00* (2006.01)

(52) U.S. Cl.
CPC ...... *A61B 17/3423* (2013.01); *A61B 17/3474* (2013.01); *A61B 17/3496* (2013.01); *A61B 17/3498* (2013.01); *A61B 2017/00951* (2013.01); *A61B 2017/3413* (2013.01); *A61B 2017/3492* (2013.01); *A61B 2217/005* (2013.01)

(58) Field of Classification Search
CPC ............ A61B 17/3423; A61B 17/3474; A61B 17/3496; A61B 17/3498; A61B 2017/00951; A61B 2017/3413; A61B 2017/3492; A61B 2217/005; A61B 17/3462; A61B 17/34; A61B 2017/00561; A61B 2017/00566; A61B 2017/308; A61B 2017/348; A61M 5/425; A61M 5/427

See application file for complete search history.

(56) References Cited

U.S. PATENT DOCUMENTS

| | | | |
|---|---|---|---|
| 4,593,947 | A | 6/1986 | Yocum |
| 5,336,206 | A | 8/1994 | Shichman |
| 6,007,486 | A | 12/1999 | Hunt et al. |

(Continued)

FOREIGN PATENT DOCUMENTS

| | | |
|---|---|---|
| CN | 105852922 | 8/2016 |
| JP | 2019-506929 | 3/2019 |

(Continued)

*Primary Examiner* — Theodore J Stigell
(74) *Attorney, Agent, or Firm* — Levine Bagade Han LLP

(57) ABSTRACT

Trocar retractor apparatus and methods for use are described where an apparatus for positioning an instrument may generally include a substrate having a first surface and a second surface opposite to the first surface, an instrument positioning guide projecting from the first surface of the substrate, and one or more suction assemblies positioned along the second surface and in fluid communication with an interior of the substrate. The one or more suction assemblies may be attachable to a tissue region via a vacuum force applied through the one or more suction assemblies. The apparatus may also have the substrate configured to maintain a predetermined configuration when the vacuum force is applied.

14 Claims, 18 Drawing Sheets

(56) References Cited

U.S. PATENT DOCUMENTS

| | | |
|---|---|---|
| 6,193,652 B1 | 2/2001 | Berky et al. |
| 6,511,416 B1 | 1/2003 | Green et al. |
| 6,890,292 B2 | 5/2005 | Kochamba et al. |
| 9,237,932 B2 | 1/2016 | Ghaderi |
| 11,690,649 B2 | 7/2023 | Rimsa et al. |
| 2007/0270745 A1 | 11/2007 | Nezhat et al. |
| 2008/0015624 A1* | 1/2008 | Sonoda ............... A61M 5/425 606/185 |
| 2008/0058603 A1 | 3/2008 | Edelstein et al. |
| 2010/0041990 A1* | 2/2010 | Schlitt ............... A61B 17/3403 600/461 |
| 2010/0210915 A1 | 8/2010 | Caldwell et al. |
| 2014/0316379 A1 | 10/2014 | Sonderegger et al. |
| 2015/0230868 A1 | 8/2015 | Miller |
| 2016/0051279 A1 | 2/2016 | Haraga et al. |
| 2017/0196590 A1 | 7/2017 | Sperry et al. |
| 2018/0310975 A1 | 11/2018 | Haufe et al. |
| 2019/0053825 A1 | 2/2019 | Ochoa |
| 2021/0177457 A1 | 6/2021 | Rimsa et al. |
| 2021/0177460 A1 | 6/2021 | Rimsa et al. |

FOREIGN PATENT DOCUMENTS

| | | |
|---|---|---|
| WO | WO 2014/157450 | 2/2017 |
| WO | WO 2019/200299 | 10/2019 |
| WO | WO 2021/118828 | 6/2021 |

\* cited by examiner

TROCAR POSITIONING APPARATUS AND METHODS FOR USE

CROSS-REFERENCE TO RELATED APPLICATIONS

This is a divisional of U.S. application Ser. No. 16/993,779 filed Aug. 14, 2020 (now U.S. Pat. No. 11,871,961), which claims the benefit of priority to U.S. Prov. App. 62/948,050 filed Dec. 13, 2019, each of which is incorporated herein by reference in its entirety.

FIELD OF THE INVENTION

The present invention relates generally to medical devices and methods. More particularly, the present invention relates to apparatus and methods for the positioning of trocar devices and tissue regions.

BACKGROUND OF THE INVENTION

Trocars are typically used for surgical procedures, such as laparoscopic procedures, in order to gain access to interior body lumens through the skin surface. Generally, the trocar includes an obturator which may be blunt or sharpened which may be inserted through a hollow cannula. By inserting the trocar through the skin surface and into the body lumen, such as an abdominal cavity, the obturator may be removed from the cannula leaving an access pathway through the cannula and into the body lumen. Unfortunately, trocars typically do not provide any indication of trocar penetration depth to the user who must estimate the penetration depth during and after penetration of the abdominal wall.

Furthermore, trocar insertion can lead to a perforating puncture wound of an underlying organ or structure resulting in a medical complication. For instance, laparoscopic intra-abdominal trocar insertion can lead to injury of the underlying bowels or to hemorrhaging of various blood vessels. This is further complicated by the tendency of the tissue to collapse or depress around the trocar when the trocar is inserted into the tissue.

To reduce the incidence of unintentional perforation, surgeons may establish a pneumoperitoneum by insufflating the abdomen with a gas to expand the space between the interior of the abdominal wall and underlying internal organs with the intention of providing a space for a trocar to penetrate through the abdominal wall and above the organs. The pneumoperitoneum is typically established through the use of a Veress needle which is used to penetrate the abdominal cavity and deliver the gas but the needle also has the same potential complications as trocar insertion.

Once penetration of the body wall has been attained, the obturator may be removed, leaving a cannula penetrating the body adapted to receive any number of surgical instruments. However, the guide tube may be subject to unintentional or undesirable movements such as changes in penetration depth or accidental withdrawal from the body.

Therefore, there exists a need for an insufflation/trocar device which can be inserted safely into a patient body with a reduced risk of underlying tissue injury. There is also a need for devices which allow for the positioning and retraction of tissue regions during procedures without risk of injury or inadvertent movement.

SUMMARY OF THE INVENTION

One variation of a trocar positioning platform which may also be used for tissue retraction or positioning. The positioning platform may include a substrate having a first side upon which a trocar positioning guide may extend and a second side which is configured to apply a releasable vacuum through one or more suction openings which may be adhered upon a tissue surface for temporary securement. A pump or negative pressure mechanism located remotely from the substrate may be fluidly coupled to the substrate via one or more fluid lines for providing the vacuum force. The one or more suction openings may be distributed over the substrate in a uniform manner, an arbitrary manner, or in any number of predetermined specified configurations. The one or more suction openings may each define a chamber defined by an individual suction assembly. While the number of suction openings may vary from one to a plurality of openings, one variation of the substrate may incorporate, e.g., twenty-one to twenty-five suction openings.

The substrate may be formed to have any variety of configurations (e.g., circular, elliptical, rectangular, pentagonal, hexagonal, octagonal, etc.) so long as the substrate is desirably positionable upon a tissue region of interest. While the substrate may be formed in a number of different configurations, the variation shown may be comprised of a first flexible layer and a second flexible layer positioned opposite to the first layer such that a securement layer is formed therebetween and the first and second layers are free to slide relative to one another. The first and second layers may be secured or otherwise sealed to one another around their periphery such that the securement layer between is formed into an air-tight chamber in fluid communication with each of the one or more suction openings. The securement layer may be filled completely or at least partially with a material which restricts the sliding movement between the first and second layers such as a screen, mesh, beads, grooves, channels which are transverse or angled relative to one another, projections on opposed surfaces, etc. or any substance or feature which increases the frictional resistance between the first and second layers. In the event that a mesh layer is used as a securement layer, there is no minimum thickness or porosity that the mesh may have so long as the mesh provides sufficient frictional resistance to movement between the first and second layers when collapsed by the vacuum force.

During initial positioning of the substrate against a tissue region, the first and second layers may freely slide relative to one another as well as relative to the securement layer thereby allowing for the substrate to conform against the anatomy of the underlying adhered tissue. Once a vacuum force is applied via a fluidly coupled vacuum line through the substrate, e.g., 600 to 650 mmHg, the one or more suction openings may attach to the underlying tissue due to the negative pressure and the first and second layers may collapse upon or towards one another. The presence of the securement layer may increase the frictional resistance between the contacting inner surfaces of the first and second layers against one another and against the securement layer such that the substrate may become frozen in its reconfigured shape. If the substrate were reconfigured to conform to an anatomy of the underlying tissue or reconfigured into another shape, application of the negative pressure may collapse the first and second layers such that substrate may maintain its configuration while the vacuum is applied. If the substrate were adhered against the underlying tissue in a flattened configuration, application of the negative pressure may collapse the first and second layers such that the flattened configuration is maintained. Once the vacuum force is released or the pressure increased, the first and second layers may release from one another and from the securement layer enabling the substrate to release from the tissue and revert to its flexible shape for removal or attachment to the tissue or to another region of tissue.

The substrate may further define one or more channels or openings which may extend from a periphery of the substrate towards the insufflation/trocar positioning guide to further provide for flexibility of the substrate. Moreover, the trocar positioning guide may project from the substrate, e.g., transversely or at an angle relative to the substrate, such that the positioning guide comprises a trocar channel which defines a lumen passing through the substrate to allow for the trocar to pass through and into the underlying tissue. The positioning guide may also have a shoulder which projects radially from a proximal portion of the trocar channel which provides a handle for ease of manipulation and adjustment of the positioning guide and substrate by the user and which also facilitates the insertion of the trocar into the trocar channel. The trocar channel may further define an opening or slit along the channel to provide for angled positioning of the trocar in a controlled manner relative to the substrate and trocar positioning guide. Hence, the width of the opening or slit along the trocar channel may have a dimension which is the same or slightly larger than the diameter of the trocar itself. Moreover, there may be a plurality of interchangeable guides for specific applications or procedures to improve access or retraction such as retraction for tissue positioning, insufflation, trocar placement, or facia closure.

In one example of use, the platform may be positioned over a tissue region of interest to be treated and the one or more suction openings may be placed into contact upon the tissue, e.g., skin surface, such that the positioning guide projects away from the skin surface. A vacuum force may be actuated via a pump fluidly coupled via one or more fluid lines and applied through the substrate such that the one or more suction openings create an adhesion force to secure the substrate upon the skin surface. The substrate may be positioned to ensure that the opening of the positioning guide is aligned directly over the portion of the tissue to be pierced by the trocar.

With the positioning platform so positioned, the trocar may be advanced through the positioning guide with an insertion force applied to the trocar and towards the tissue region to be entered. Simultaneously, a counterforce may be applied directly to the positioning guide in the opposite direction of the insertion force. With the tissue adhered to the one or more suction openings and with the counterforce applied in the opposing direction of the insertion force from the trocar, the tissue may be maintained in a relatively neutral state as the trocar is inserted through the skin surface and further into the tissue. That is, the tissue may be prevented from dimpling or collapsing further into the body as the trocar is initially inserted and advanced into the tissue. This may further prevent the inadvertent insertion, damage, or nicking of tissue structures during trocar insertion. After the trocar has been inserted into the tissue, the vacuum level may be optionally reduced from an initial level.

Another variation of the positioning platform may utilize a substrate formed from any number of biocompatible flexible materials (e.g., polyethylene, polyvinyl, silicone, etc.) which are configured to have an adhesive surface for temporary securement to a skin surface. With the positioning guide extending from the first surface, the second surface may be coated or infused with any number of biocompatible agents or adhesives (e.g., acrylates, cyanoacrylates, silicone, polyurethane, epoxy, etc.) which may temporarily adhere the second surface to the tissue surface. While the substrate may not be adhered via a vacuum force which collapses layers of the substrate to maintain a shape or configuration, the substrate may still be used to retract the tissue once adhered as well as reconfigure the tissue, for example, by manually reconfiguring the tissue region. Furthermore, this variation may also optionally incorporate a pivoting or redirectable positioning guide with the substrate.

Yet another variation may utilize a handle secured to the first side of the substrate. This variation may omit a trocar positioning guide and opening such that positioning platform is used as a tissue retractor or manipulator once the substrate is adhered to the tissue surface. The handle may be configured into any number of configurations which allow for the user to manipulate the substrate into various positions.

Yet another variation may have a substrate incorporate a handle projecting from a first side of the substrate. The second surface of the substrate may be configured to have, e.g., an adhesive (as described herein), for temporary attachment to a tissue surface. The interior of the substrate may be filled with a particulate material such as beads (made from any variety of materials such as plastics, polymers, etc.) which are free to move relative to one another and contained between the first layer and second layer of the substrate. The beads are freely movable prior to the interior being collapsed by a vacuum force such that the substrate, when placed upon a tissue surface, may conform to the anatomy. Once adhered to the tissue surface in its unconstrained configuration where the beads are freely movable, the substrate may be reconfigured via manipulation of the handle, for instance, to retract the tissue region of interest. The vacuum force may be applied to the interior of the substrate while holding the handle in its reconfigured shape until the layers collapse against one another and upon the contained beads. The beads may collapse against one another increasing the frictional resistance and forcing the substrate to maintain its reconfigured shape and also forcing the adhered tissue to maintain the same reconfigured shape, e.g., remaining in a retracted state. Once the vacuum force is removed and air is allowed to re-enter the interior of substrate, the substrate may relax is shape and allow for the adhered tissue to flatten or return to its initial shape.

One variation for an apparatus for positioning an instrument may generally comprise a substrate having a first surface and a second surface opposite to the first surface, an instrument positioning guide projecting from the first surface of the substrate, and one or more suction assemblies positioned along the second surface and in fluid communication with an interior of the substrate, wherein the one or more suction assemblies are attachable to a tissue region via a vacuum force applied through the one or more suction assemblies. The apparatus may have the substrate configured to maintain a predetermined configuration when the vacuum force is applied.

One variation for a method of positioning the instrument may generally comprise positioning a second surface of a substrate in proximity to a tissue surface, where the second surface is opposite to a first surface of the substrate, adhering one or more suction assemblies positioned along the second surface to the tissue surface via a vacuum force applied through the one or more suction assemblies, wherein the one or more suction assemblies are in fluid communication with an interior of the substrate, advancing an instrument through or along an instrument positioning guide projecting from the first surface of the substrate and into the tissue surface, and applying a counterforce to the substrate while advancing the instrument into the tissue surface.

Another variation for a method of positioning the instrument may generally comprise positioning a second surface of a substrate in proximity to a tissue surface, where the second surface is opposite to a first surface of the substrate, adhering one or more suction assemblies positioned along the second surface to the tissue surface via a vacuum force applied through the one or more suction assemblies, wherein the one or more suction assemblies are in fluid communication with an interior of the substrate, reconfiguring a shape of the substrate while adhering the tissue surface to the one or more suction assemblies such that the tissue surface is reconfigured accordingly, advancing an instrument through or along an instrument positioning guide projecting from the first surface of the substrate and into the tissue surface, and applying a counterforce to the substrate while advancing the instrument into the tissue surface.

Yet another apparatus for retracting a tissue region may generally comprise a substrate having a first surface and a second surface opposite to the first surface, one or more suction assemblies positioned along the second surface and in fluid communication with an interior of the substrate, wherein the one or more suction assemblies are attachable to the tissue region via a vacuum force applied through the one or more suction assemblies, and wherein the substrate is configured to maintain a predetermined configuration when the vacuum force is applied.

Yet another method of positioning an instrument may generally comprise positioning a second surface of a substrate in proximity to a tissue surface, where the second surface is opposite to a first surface of the substrate, adhering one or more suction assemblies positioned along the second surface to the tissue surface via a vacuum force applied through the one or more suction assemblies, wherein the one or more suction assemblies are in fluid communication with an interior of the substrate, and maintaining a first configuration of the substrate via the vacuum force such that the adhered tissue surface conforms to the first configuration.

For all embodiments, it is anticipated that the amount of vacuum required may vary upon the procedure. For example, a higher vacuum level may be required during retraction while a lower vacuum may be required for maintaining position on the tissue, and/or maintaining tissue/trocar orientation. This may be achieved through, e.g., direct adjustment of the vacuum level at the source or a user activated valve which may be integrated into the device itself that may provide variable or preset levels of vacuum.

DETAILED DESCRIPTION OF THE INVENTION

In accessing regions within a subject's body, trocar devices are typically used to provide access for various surgical instruments such as laparoscopic instruments. During the initial insertion of the trocar through the skin and tissue layers, there is risk that the trocar may unintentionally damage underlying tissue. Moreover, once inserted through the skin surface and into the patient body, the trocar and/or instruments may be desirably repositioned or angled relative to the underlying tissue. Additionally, during a surgical procedure, the tissue underlying the skin may be desirably retracted or moved temporarily to facilitate the procedure being performed upon the subject.

Figure 1:
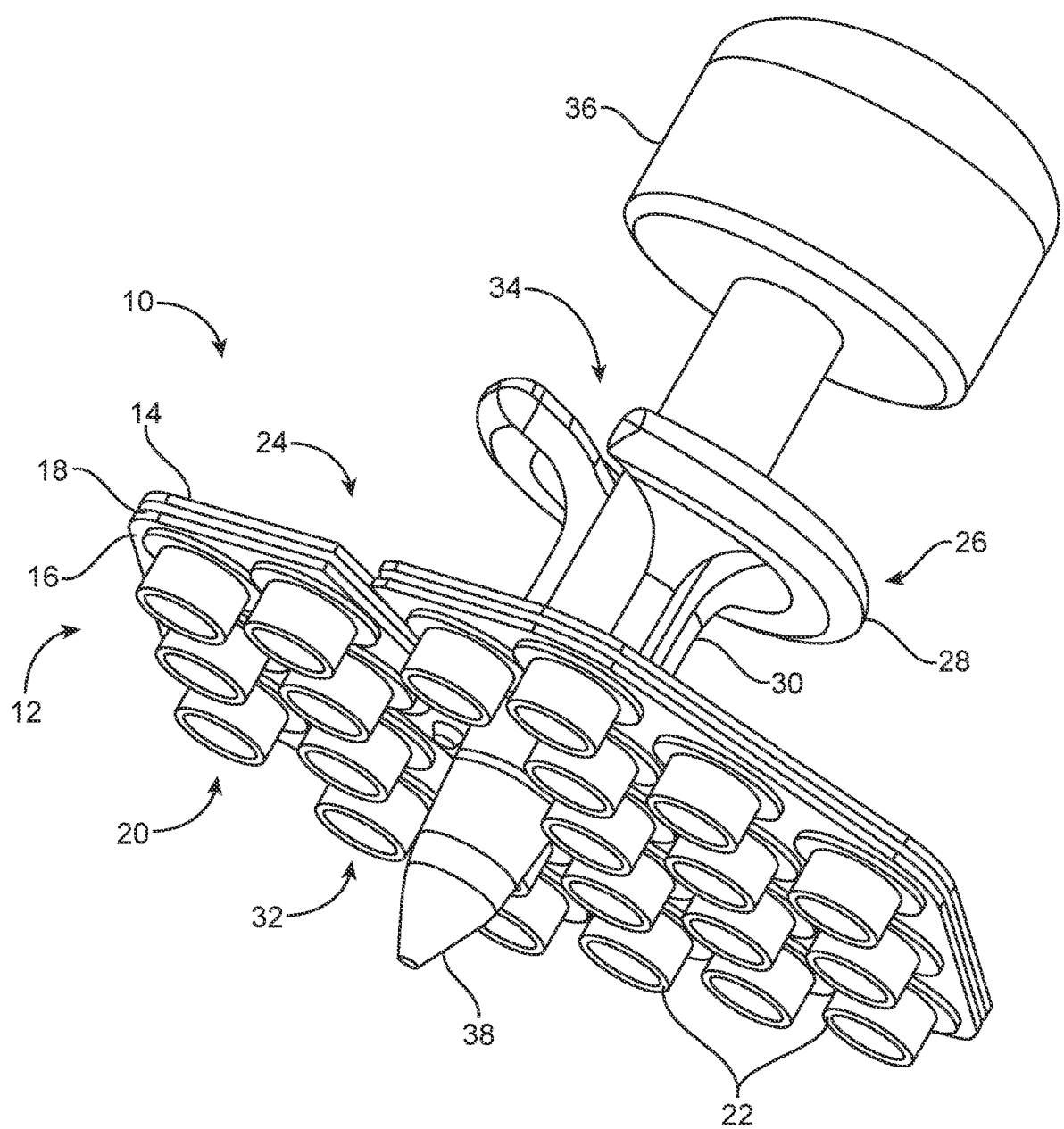
FIG. 1 shows a perspective view of one variation of the trocar positioning and retraction platform.

One variation of a trocar positioning platform which may also be used for tissue retraction or positioning is shown in the perspective view of FIG. 1. The positioning platform 10 is shown as substrate 12 having a first side upon which a trocar positioning guide 26 may extend and a second side which is configured to apply a releasable vacuum through one or more suction openings 20 which may be adhered upon a tissue surface for temporary securement. A pump or negative pressure mechanism located remotely from the substrate 12 may be fluidly coupled to the substrate 12 via one or more fluid lines for providing the vacuum force. The one or more suction openings 20 may be distributed over the substrate 12 in a uniform manner, an arbitrary manner, or in any number of predetermined specified configurations. The one or more suction openings 20 may each define a chamber defined by an individual suction assembly 22. While the number of suction openings 20 may vary from one to a plurality of openings, one variation of the substrate 12 may incorporate, e.g., twenty-one to twenty-five suction openings.

The substrate 12 may be formed to have any variety of configurations (e.g., circular, elliptical, rectangular, pentagonal, hexagonal, octagonal, etc.) so long as the substrate 12 is desirably positionable upon a tissue region of interest. While the substrate 12 may be formed in a number of different configurations, the variation shown may be comprised of a first flexible layer 14 and a second flexible layer 16 positioned opposite to the first layer 14 such that a securement layer 18 is formed therebetween and the first and second layers 14, 16 are free to slide relative to one another. The first and second layers 14, 16 may be secured or otherwise sealed to one another around their periphery such that the securement layer 18 between is formed into an air-tight chamber in fluid communication with each of the one or more suction openings 20. The securement layer 18 may be filled completely or at least partially with a material which restricts the sliding movement between the first and second layers 14, 16 such as a screen, mesh, beads, grooves, channels which are transverse or angled relative to one another, projections on opposed surfaces, etc. or any substance or feature which increases the frictional resistance between the first and second layers 14, 16. In the event that a mesh layer is used as a securement layer 18, there is no minimum thickness or porosity that the mesh may have so long as the mesh provides sufficient frictional resistance to movement between the first and second layers 14, 16 when collapsed by the vacuum force.

During initial positioning of the substrate against a tissue region, the first and second layers 14, 16 may freely slide relative to one another as well as relative to the securement layer 18 thereby allowing for the substrate 12 to conform against the anatomy of the underlying adhered tissue. Once a vacuum force is applied via a fluidly coupled vacuum line through the substrate 12, e.g., 600 to 650 mmHg, the one or more suction openings 20 may attach to the underlying tissue due to the negative pressure and the first and second layers 14, 16 may collapse upon or towards one another. The presence of the securement layer 18 may increase the frictional resistance between the contacting inner surfaces of the first and second layers 14, 16 against one another and against the securement layer 18 such that the substrate 12 may become frozen in its reconfigured shape. If the substrate 12 were reconfigured to conform to an anatomy of the underlying tissue or reconfigured into another shape, application of the negative pressure may collapse the first and second layers 14, 16 such that substrate 12 may maintain its configuration while the vacuum is applied. If the substrate 12 were adhered against the underlying tissue in a flattened configuration, application of the negative pressure may collapse the first and second layers 14, 16 such that the flattened configuration is maintained. Once the vacuum force is released or the pressure increased, the first and second layers 14, 16 may release from one another and from the securement layer 18 enabling the substrate 12 to release from the tissue and revert to its flexible shape for removal or attachment to the tissue or to another region of tissue.

The substrate 12 may further define one or more channels or openings 24 which may extend from a periphery of the substrate 12 towards the trocar positioning guide 26 to further provide for flexibility of the substrate 12. Moreover, the trocar positioning guide 26 may project from the substrate 12, e.g., transversely or at an angle relative to the substrate 12, such that the positioning guide 26 comprises a trocar channel 30 which defines a lumen 32 passing through the substrate 12 to allow for the trocar 36 to pass through and into the underlying tissue. The trocar 36 may be seen extending through the trocar channel 30 such that the trocar distal tip 38 has been pushed through past the substrate 12 and into the underlying tissue. The positioning guide 26 may also have a shoulder 28 which projects radially from a proximal portion of the trocar channel 30 which provides a handle for ease of manipulation and adjustment of the positioning guide 26 and substrate 12 by the user and which also facilitates the insertion of the trocar 36 into the trocar channel 30. The trocar channel 30 may further define an opening or slit 34 along the channel 30 to provide for angled positioning of the trocar 36 in a controlled manner relative to the substrate 12 and trocar positioning guide 26. Hence, the width of the opening or slit 34 along the trocar channel 30 may have a dimension which is the same or slightly larger than the diameter of the trocar 36 itself.

Figure 2A:
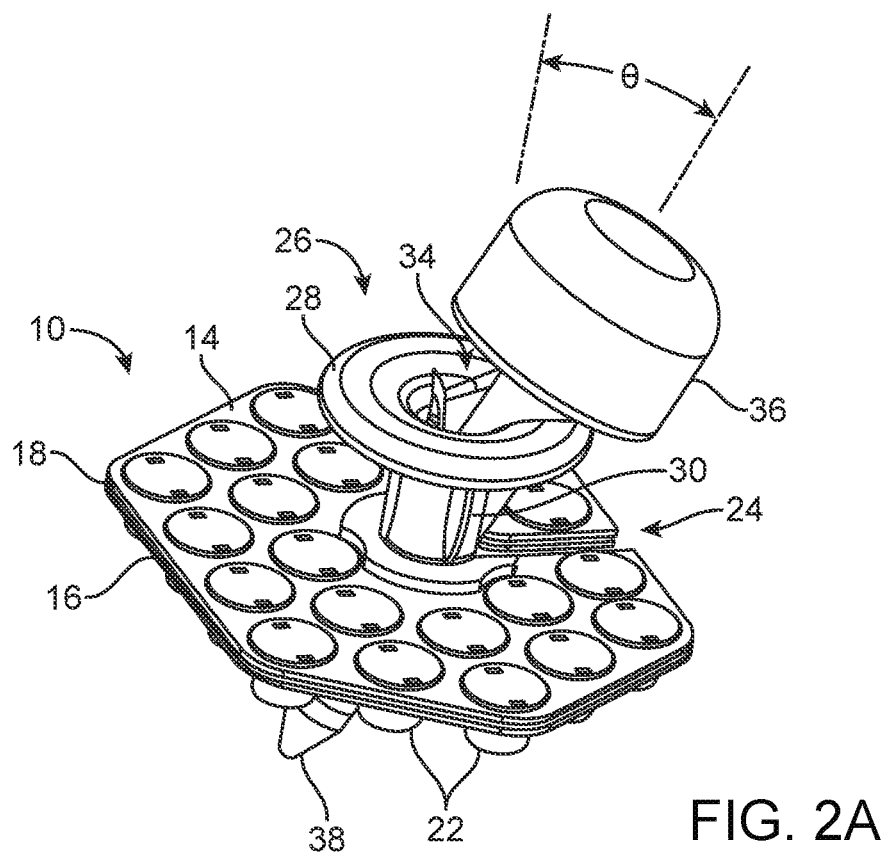
FIGS. 2A and 2B show perspective and side views of the trocar positioning and retraction platform with the trocar angled relative to the platform.
Figure 2B:
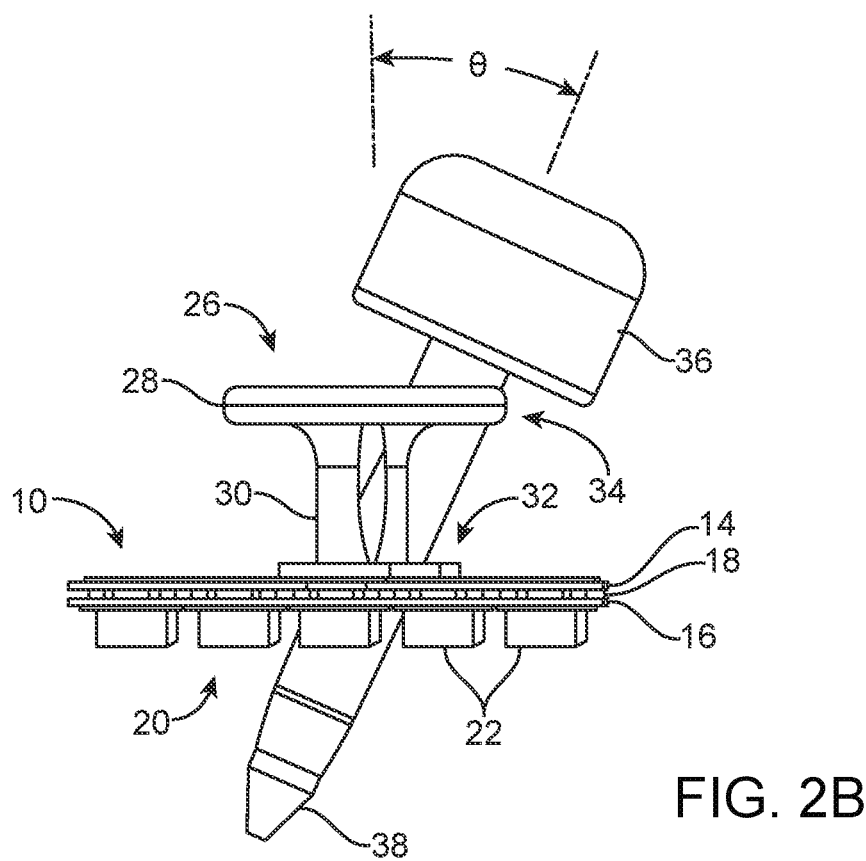

FIGS. 2A and 2B show perspective and side views of the substrate 12 and the trocar 36 angled relative to the substrate 12. With the substrate 12 adhered against the tissue surface, the trocar 36 may be inserted at an angle relative to the substrate 12 and/or tissue surface or the trocar 36 may be angled after insertion such that the body of the trocar 36 is positioned within or along the opening or slit 34 defined along the channel 30. In either case, the trocar 36 may be positioned at an angle θ such that a longitudinal axis of the trocar 36 is angled relative to a longitudinal axis of the positioning guide 26. The angle θ may range anywhere from, e.g., 0 degrees to close to 90 degrees, depending upon the desired positioning of the trocar 36. While the positioning guide 26 is illustrated as having a channel 30, other variations of the positioning guide 26 may include other pivoting mechanisms, such as a ball pivot, etc.

Figure 3A:
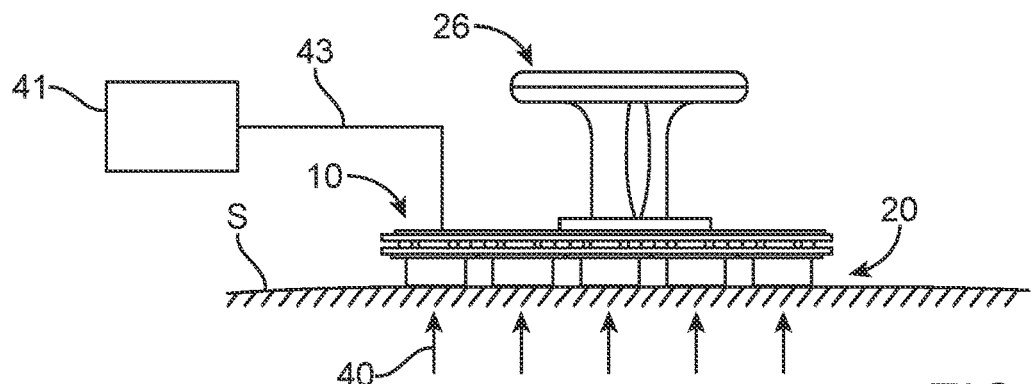
FIGS. 3A to 3C show side views of one example of how the platform may be used to provide a counterforce to the trocar during insertion through tissue.
Figure 3B:
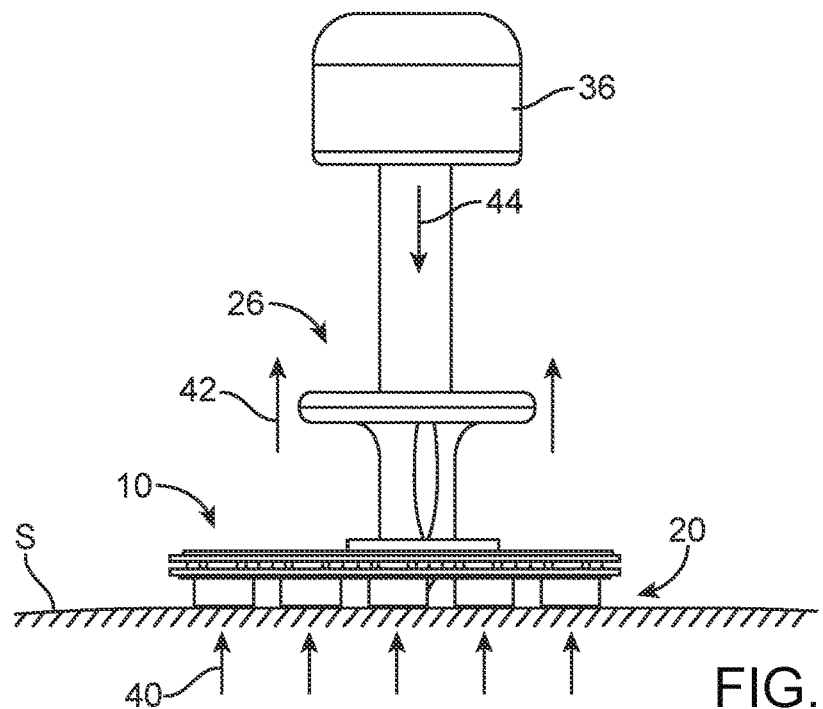
Figure 3C:
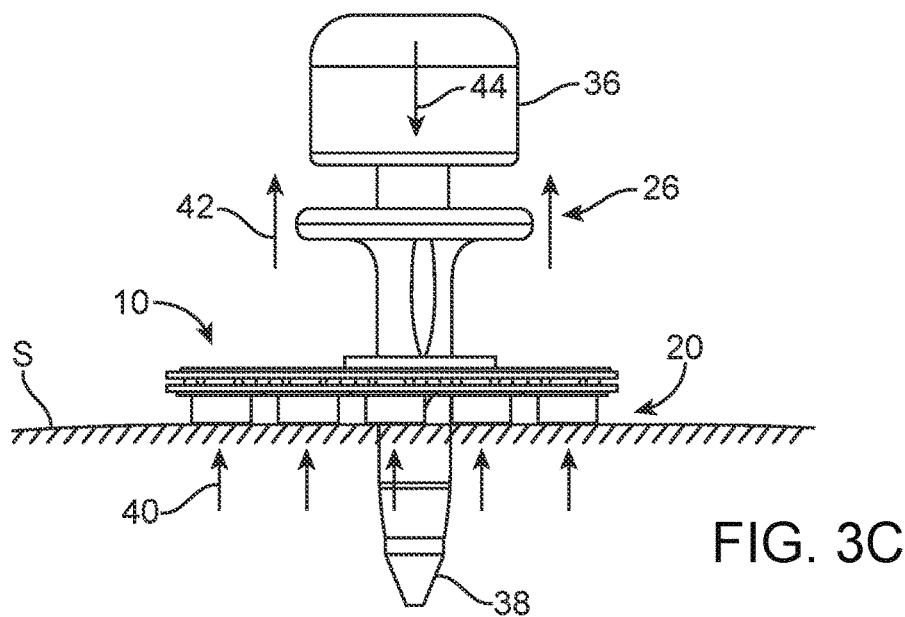

One example is illustrated in the side views of FIGS. 3A to 3C showing how the trocar positioning platform 10 may be used for tissue retraction during insertion of a trocar 36 into a tissue region of interest. As shown in FIG. 3A, the platform 10 may be positioned over a tissue region of interest to be treated and the one or more suction openings 20 may be placed into contact upon the tissue, e.g., skin surface S, such that the positioning guide 26 projects away from the skin surface S, as shown. A vacuum force may be actuated via pump 41 fluidly coupled via one or more fluid lines 43 and applied through the substrate 12 such that the one or more suction openings 20 create an adhesion force 40 to secure the substrate 12 upon the skin surface S. The substrate 12 may be positioned to ensure that the opening of the positioning guide 26 is aligned directly over the portion of the tissue to be pierced by the trocar 36.

With the positioning platform 10 so positioned, the trocar 36 may be advanced through the positioning guide 26 with an insertion force 44 applied to the trocar 36 and towards the tissue region to be entered. Simultaneously, a counterforce 42 may be applied directly to the positioning guide 26 in the opposite direction of the insertion force 44, as shown in FIG. 3B. With the tissue adhered to the one or more suction openings 20 and with the counterforce 42 applied in the opposing direction of the insertion force 44 from the trocar 36, the tissue may be maintained in a relatively neutral state as the trocar 36 is inserted through the skin surface S and further into the tissue, as shown in FIG. 3C. That is, the tissue may be prevented from dimpling or collapsing further into the body as the trocar 36 is initially inserted and advanced into the tissue. This may further prevent the inadvertent insertion, damage, or nicking of tissue structures during trocar 36 insertion. After the trocar 36 has been inserted into the tissue, the vacuum level may be optionally reduced from an initial level.

As the trocar 36 is inserted into and through the tissue, the relatively large diameter of the trocar 36 can "tent" the tissue inwardly into the patient when the point of the trocar 36 is pressed through the abdomen. The amount of tenting may dramatically increase the force required to place the trocar 36 but because the practitioner not only lifts the tissue (to also help move any internal organs out of the way) tenting of the tissue is also minimized thus requiring less force to insert the trocar 36 and also reducing the possibility of over inserting the trocar 36 into the patient body as the trocar 36 breaks into the peritoneum.

In the event that a pivoting positioning guide (as described herein) is utilized with the substrate 12, the positioning guide may be reoriented before, during, or after insertion and/or advancement of the trocar 36 into the tissue to redirect the trocar insertion into the tissue.

In one variation, the trocar 36 may be advanced using one hand of the user while the positioning guide 26 is retracted by the other hand of the user. In other variations, both the insertion and advancement of the trocar 36 as well as the retraction of the positioning guide 26 may be performed by a single hand of the user. In yet other variations, both the insertion of the trocar 36 and the retraction of the positioning guide 26 may be performed by different users.

The tissue surface S is shown in the example as remaining in a relatively flattened state during trocar 36 insertion and advancement. However, in other variations, the adhered tissue may be retracted by the positioning platform 10 and conformed by substrate 12 into a different configuration, such as a retracted configuration, which may then be maintained by the substrate 12 locking its configuration. With the altered tissue configuration, the same steps of trocar 36 insertion and advancement with retraction of the positioning guide 26 may be performed, as described.

Figure 3D:
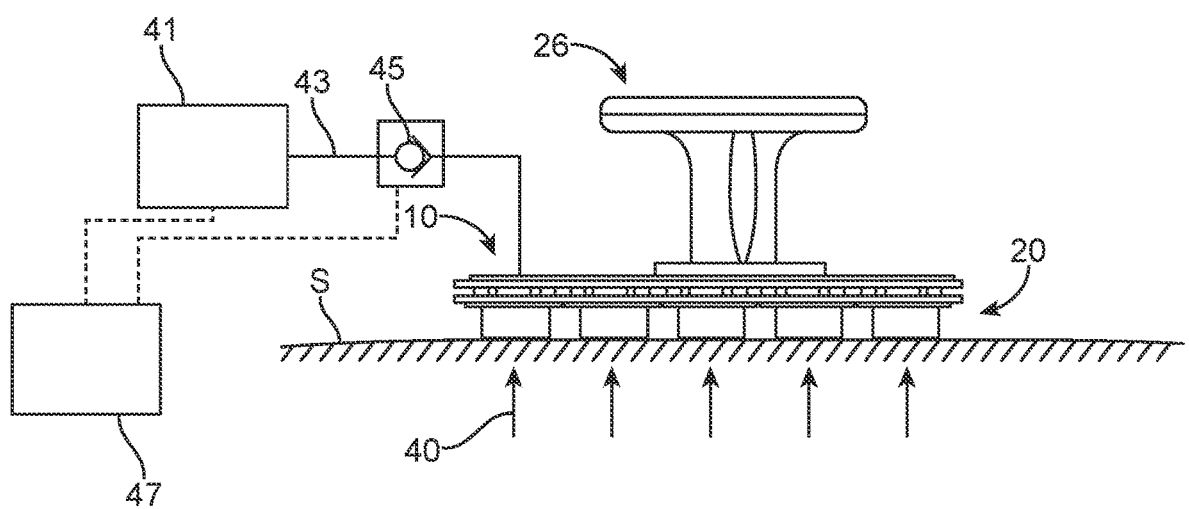
FIG. 3D shows a side view of the platform assembly in communication with a valve which is controllable to alter the suction force applied through the platform.

While the adhesion force 40 created by pump 41 to secure the platform 10 to the skin surface S may be maintained at a constant level prior to, during, and/or after a procedure, the adhesion force may be optionally varied as well. FIG. 3D illustrates a side view of the positioning guide 26 with one or more fluid lines 43 fluidly coupling the platform 10 to the pump 41, as previously described, but this variation may incorporate a valve 45, such as a check valve or variably controllable valve, along the one or more fluid lines 43 to control the level of suction force upon the skin surface S. The valve 45 may be manually controlled or the valve 45 may be optionally controlled by a controller 47 in communication with valve 45 and pump 41. The controller 47 may be programmed, for instance, to open and/or close the valve 45 at predetermined pressure levels or the valve 45 may be programmed to open and/or close at predetermined points of a procedure or when actuated by the user.

In yet another variation, a maximum first vacuum level may be applied during insertion of the trocar or other instrument such that the platform 10 provides for an optimal lifting force of the tissue. Once the insertion through the tissue has been completed, the vacuum force applied by platform 10 may be automatically adjusted down to a lower second vacuum level which may also prevent the formation of any bruises or hematomas which may result from the platform 10 being adhered to the skin surface.

Figure 4A:
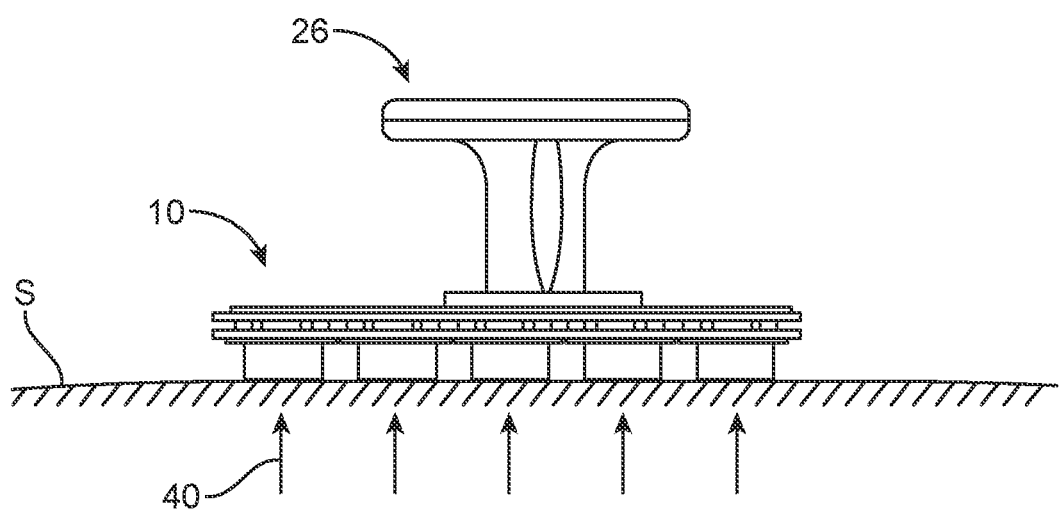
FIGS. 4A and 4B show side views of another example of how the platform may be used as a retraction device to hold a tissue region in place.
Figure 4B:
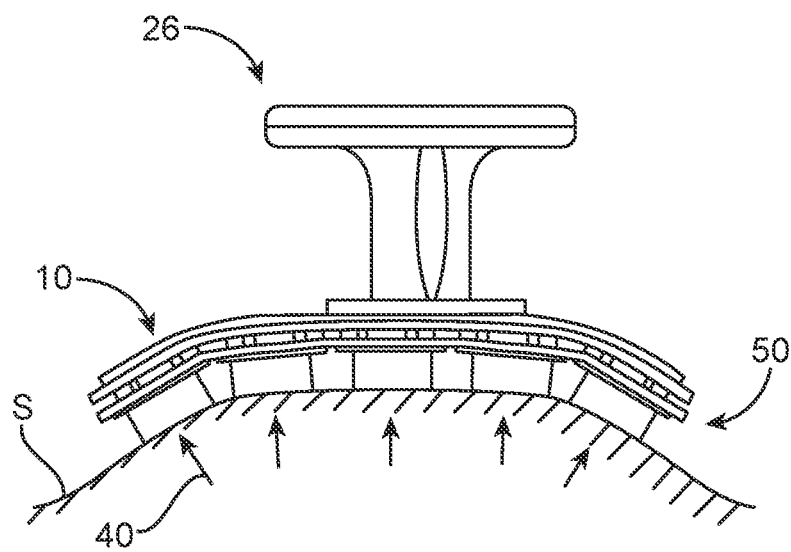

An example is illustrated in the side views of FIGS. 4A and 4B which show the positioning platform 10 placed against the tissue surface and adhered to the tissue while in a first configuration. In this variation, the positioning platform 10 may have a flattened configuration relative to the skin surface. With the one or more suction openings 20 adhered to the tissue via the adhesion force 40, the positioning guide 26 and/or substrate 12 may be retracted or moved from its initial position such that the positioning platform 10 conforms into a second configuration 50 causing the underlying adhered tissue to conform accordingly, as shown in FIG. 4B. The substrate 12 may be conformed, as described herein, to maintain this second configuration 50 to hold or maintain the adhered skin in a retracted configuration. The positioning platform 10 may be used accordingly, e.g., as an external tissue retractor, for any number of procedures such as for breast retraction.

Figure 5A:
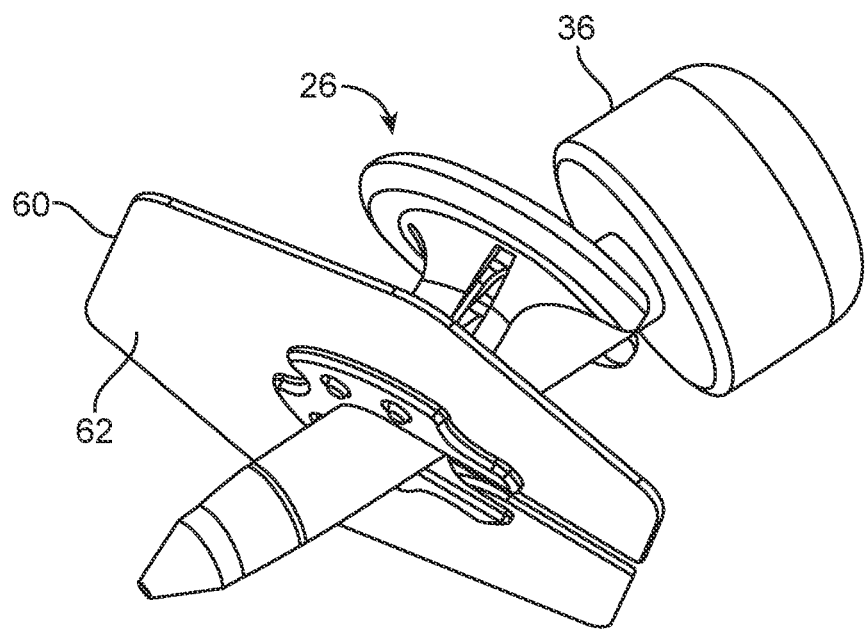
FIGS. 5A and 5B show various perspective views of yet another variation of the trocar positioning and retraction platform.
Figure 5B:
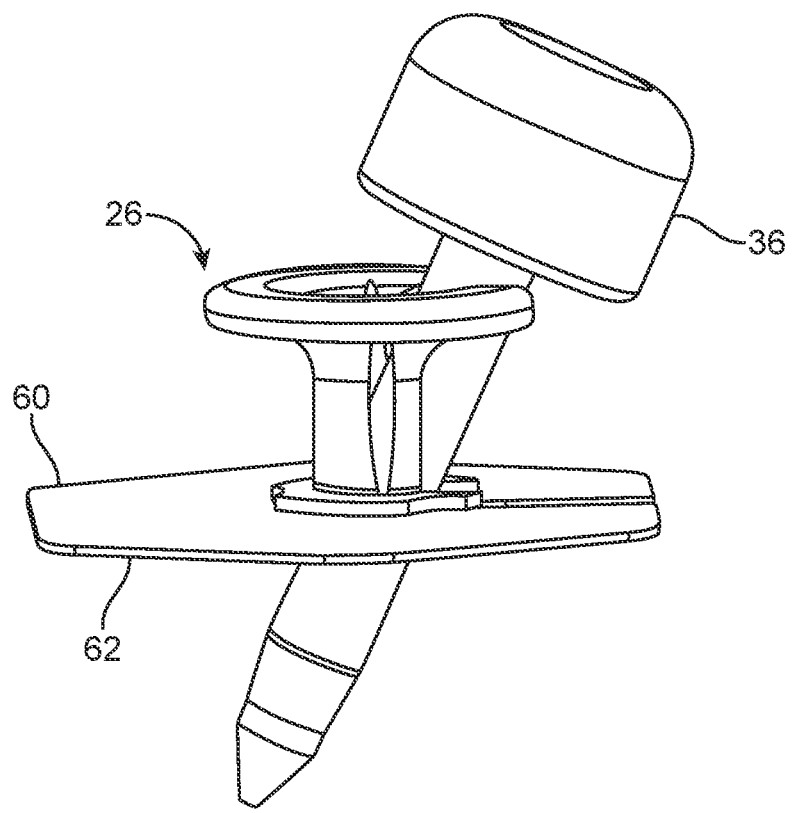

Another variation of the positioning platform is illustrated in the perspective views of FIGS. 5A and 5B. In this variation, the substrate 60 may be formed from any number of biocompatible flexible materials (e.g., polyethylene, polyvinyl, silicone, etc.) which are configured to have an adhesive surface 62 for temporary securement to a skin surface. With the positioning guide 26 extending from the first surface, the second surface 62 may be coated or infused with any number of biocompatible agents or adhesives (e.g., acrylates, cyanoacrylates, silicone, polyurethane, epoxy, etc.) which may temporarily adhere the second surface 62 to the tissue surface. While the substrate 60 may not be adhered via a vacuum force which collapses layers of the substrate to maintain a shape or configuration, the substrate 60 may still be used to retract the tissue once adhered as well as reconfigure the tissue, for example, by manually reconfiguring the tissue region. Furthermore, this variation may also optionally incorporate a pivoting or redirectable positioning guide 26 with the substrate 60.

Figure 6A:
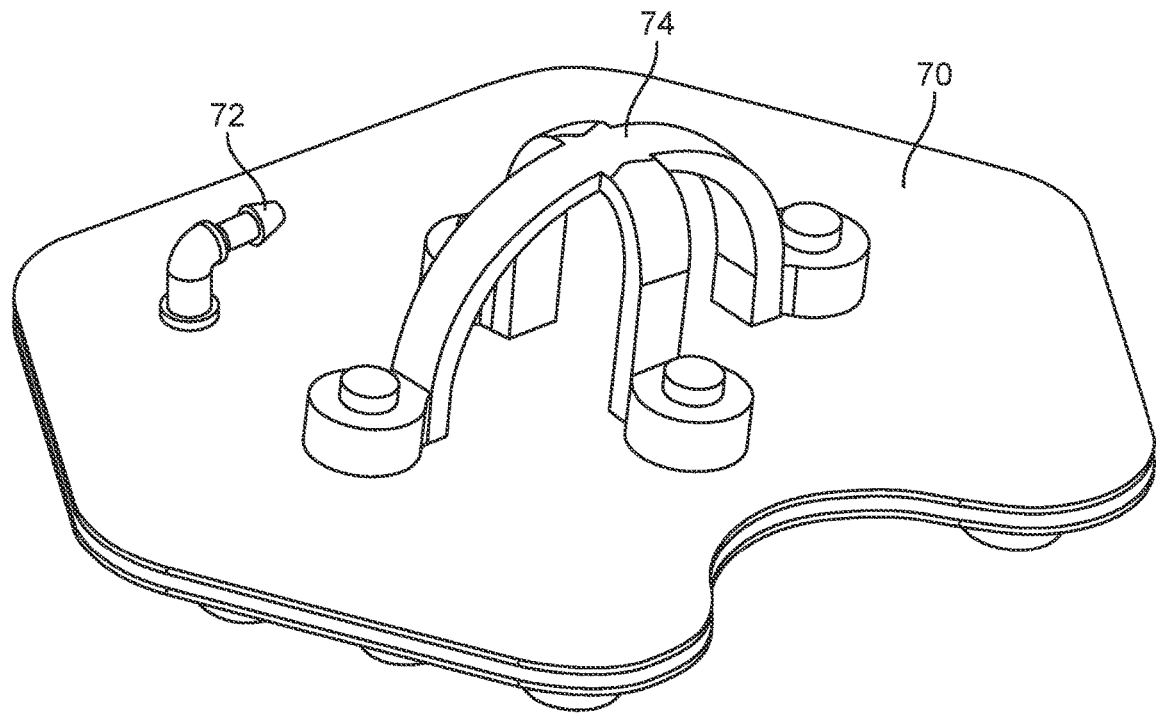
FIGS. 6A and 6B show various perspective views of yet another variation of a platform configured for tissue retraction and manipulation.
Figure 6B:
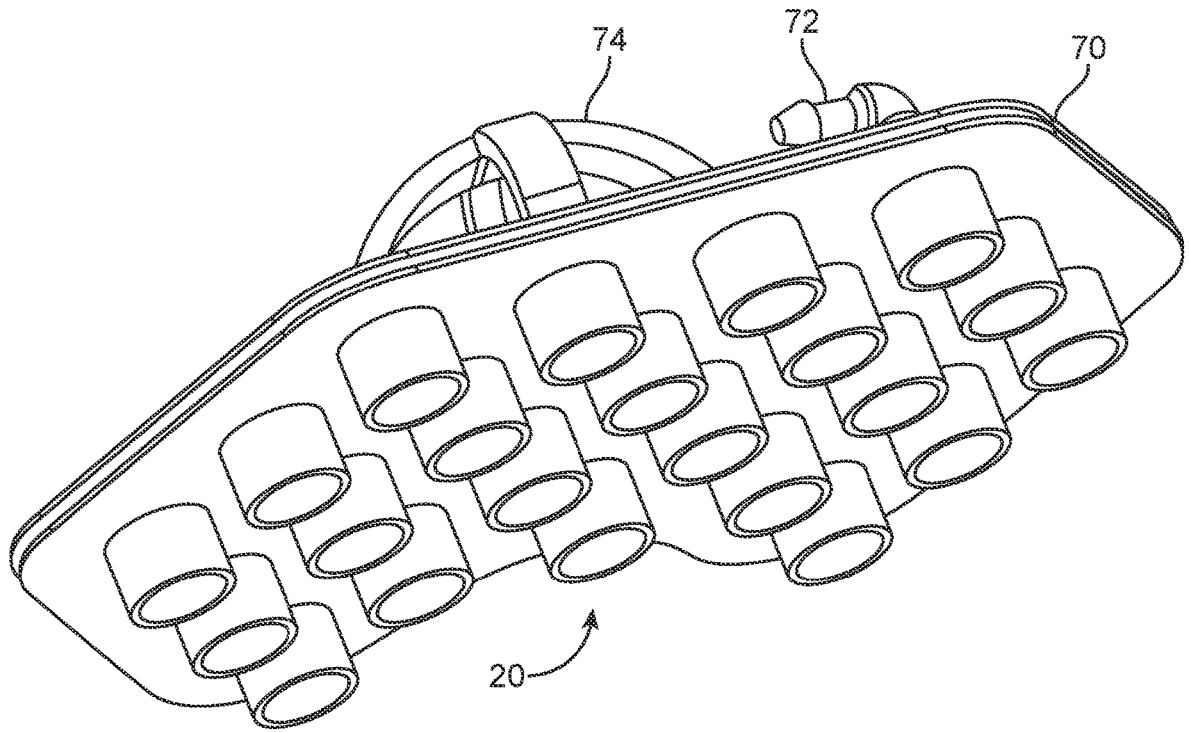

Yet another variation is shown in the perspective views of FIGS. 6A and 6B which illustrate a substrate 70 having the one or more suction openings 20 along a second side of the substrate 70 and a handle 74 secured to the first side of the substrate 70. A vacuum tube attachment 72 is illustrated as being fluidly coupled along the first side of the substrate 70. This variation may omit a trocar positioning guide 26 and opening such that positioning platform is used as a tissue retractor or manipulator once the substrate 70 is adhered to the tissue surface. The handle 74 may be configured into any number of configurations which allow for the user to manipulate the substrate 70 into various positions.

Figure 7:
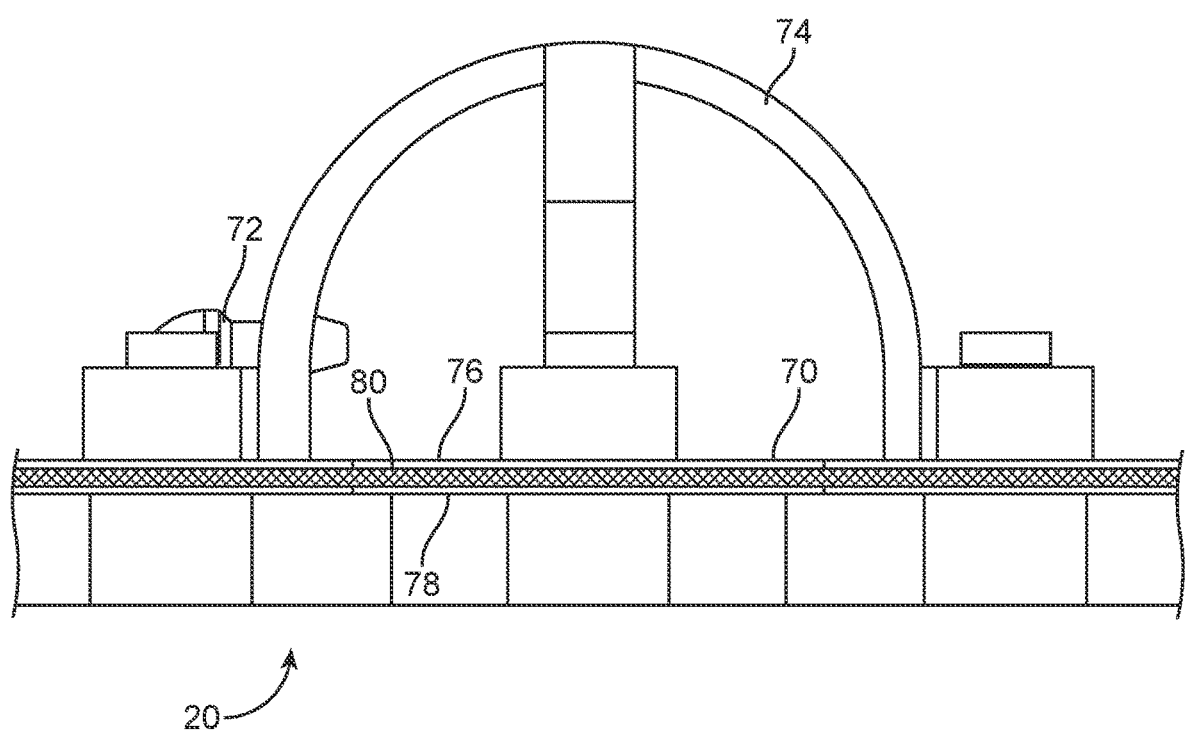
FIG. 7 shows a detail side view of the platform illustrating an example of the securement mechanism.

FIG. 7 shows a partial cross-sectional side view of the variation of FIGS. 6A and 6B to illustrate how the first layer 76 and the second layer 78 may be sealed to one another, e.g., around their periphery, to form the securement layer 80 within. As described above, the securement layer 80 may contain any number of substances or features which are designed to increase a frictional resistance between the first and second layers 76, 78 when the layers are collapsed against one another. Each of the one or more suction openings 20 may be seen as extending from the second surface and are each in fluid communication with the securement layer 80 between the first and second layers 76, 78.

Figure 8A:
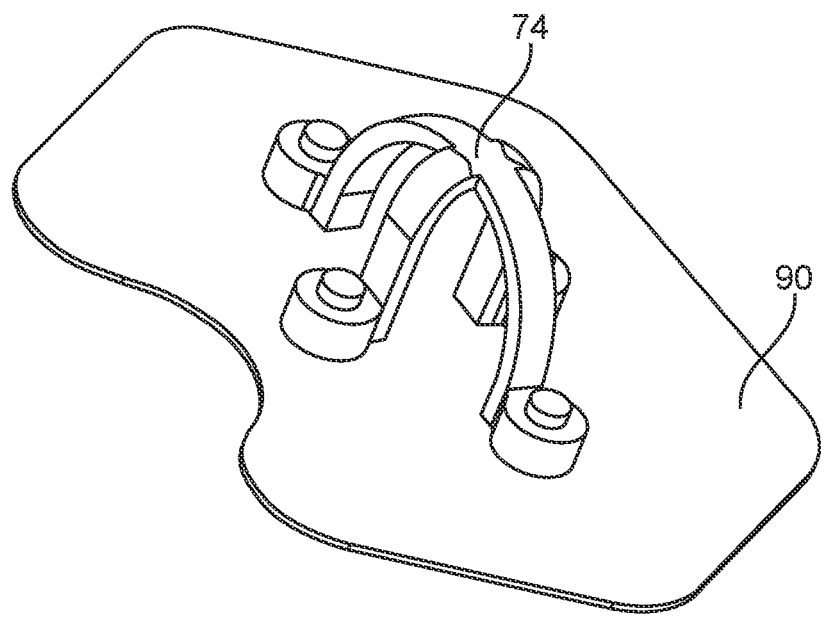
FIGS. 8A and 8B show various perspective views of yet another variation of a platform configured for tissue retraction and manipulation.
Figure 8B:
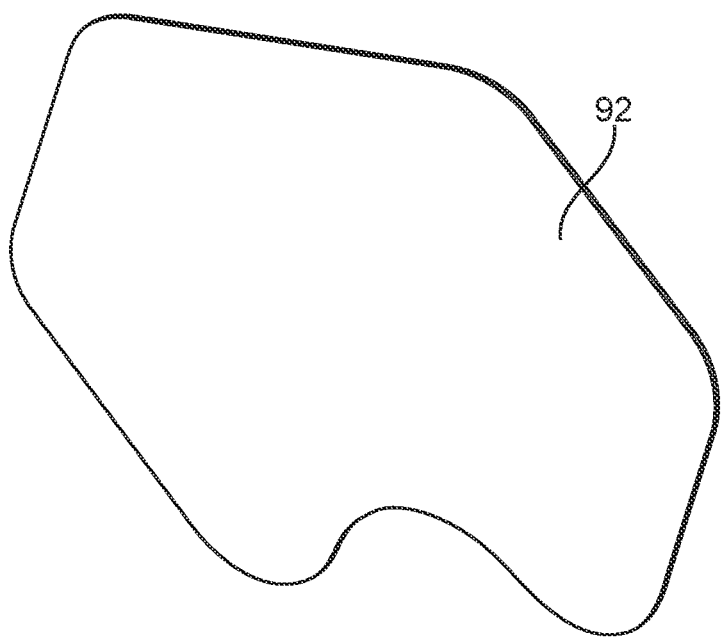

FIGS. 8A and 8B show perspective views of yet another variation of a substrate 90 which may be similar to the substrate 60 described herein. This variation may incorporate the handle 74 with the substrate 90 so that the positioning platform may be utilized, e.g., as a tissue retractor or manipulator, once adhered to the tissue surface.

Figure 9A:
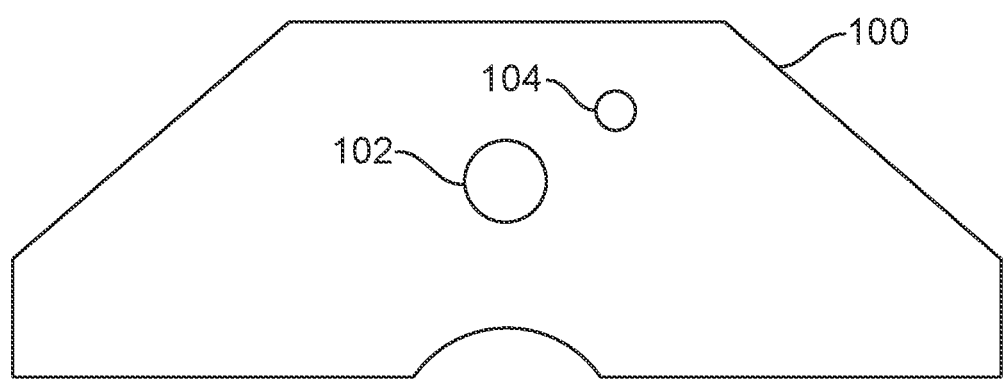
FIGS. 9A and 9B show top and side views of yet another variation of a platform configured for tissue retraction and manipulation.
Figure 9B:
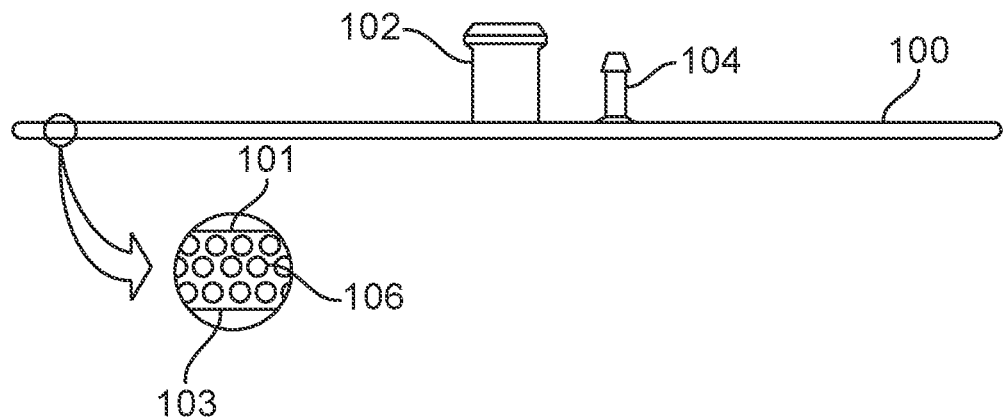
Figure 9C:
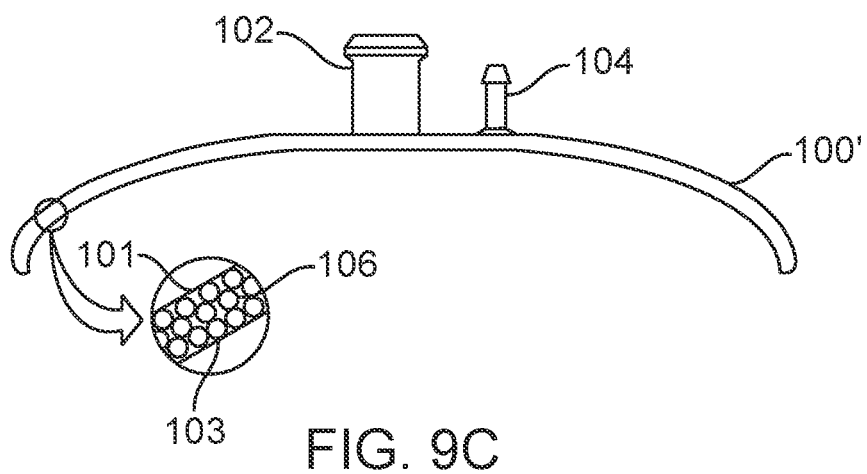
FIG. 9C shows a side view of the platform of FIGS. 9A and 9B illustrating how the platform may be reconfigured to maintain its shape against a tissue region.

Yet another variation is shown in the top and side views of FIGS. 9A to 9C which show a positioning platform configured for tissue retraction and/or manipulation. The substrate 100 in this variation may incorporate a handle 102 projecting from a first side of the substrate 100. A vacuum tube attachment 104 is also shown projecting from the first side and which is in fluid communication with the interior of the substrate, as shown in the top view of FIG. 9A. The second surface of the substrate 100 may be configured to have, e.g., an adhesive (as described herein), for temporary attachment to a tissue surface. The side view of FIG. 9B shows a detail cross-sectional view of an interior of the substrate 100 which may be filled with a particulate material such as beads 106 (made from any variety of materials such as plastics, polymers, etc.) which are free to move relative to one another and contained between the first layer 101 and second layer 103 of the substrate 100. As illustrated, the beads 106 are shown to be freely movable prior to the interior being collapsed by a vacuum force such that the substrate 100, when placed upon a tissue surface, may conform to the anatomy. Once adhered to the tissue surface in its unconstrained configuration where the beads 106 are freely movable, the substrate 100 may be reconfigured via manipulation of the handle 102, for instance, to retract the tissue region of interest. The vacuum force may be applied to the interior of the substrate 100' while holding the handle 102 in its reconfigured shape until the layers 101, 103 to collapse against one another and upon the contained beads 106, as shown in FIG. 9C. The beads 106 may collapse against one another increasing the frictional resistance and forcing the substrate 100' to maintain its reconfigured shape and also forcing the adhered tissue to maintain the same reconfigured shape, e.g., remaining in a retracted state. Once the vacuum force is removed and air is allowed to re-enter the interior of substrate 100, the substrate 100 may relax is shape and allow for the adhered tissue to flatten or return to its initial shape.

Figure 10A:
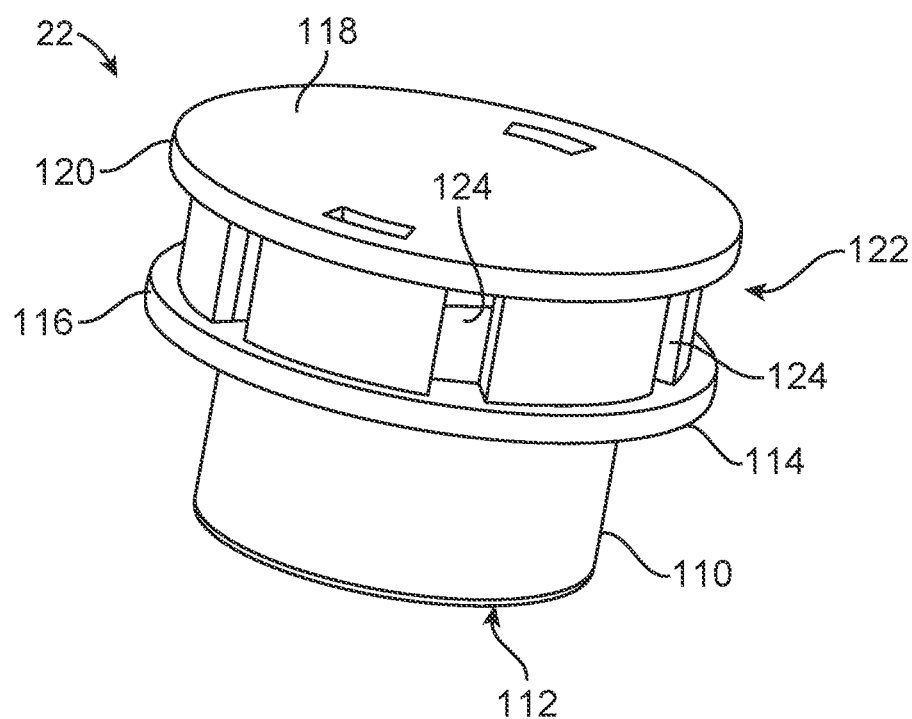
FIGS. 10A and 10B show various perspective views of an individual suction mechanism for temporary adherence to a tissue region.
Figure 10B:
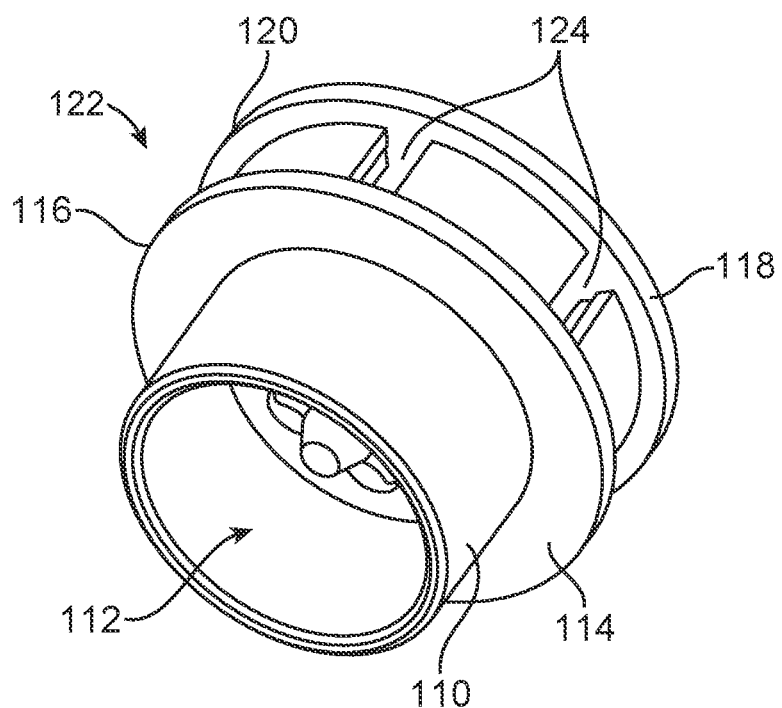

Turning now to the structure of the individual suction assembly 22, FIGS. 10A and 10B show various perspective views of one variation. The suction assembly 22 may be formed to have a suction housing 110 which projects to form a suction chamber 112 for placement against the surface of the tissue to be adhered. The suction housing 110 may define any number of cross-sectional shapes suitable for forming the suction chamber 112 (e.g., circular, elliptical, rectangular, polygonal, etc.) and may project distally from a lower housing 114 having a lower shoulder 116 which projects radially to form a lower periphery of the lower housing 114. An upper housing 118 may be attached to the lower housing 114 and may similarly have an upper shoulder 120 which projects radially to form an upper periphery of the upper housing 118. A substrate attachment portion 122 may be formed between the lower shoulder 116 and the upper shoulder 120 for attachment to the first and second layers of the substrate. Additionally, one or more fluid channels 124 may be defined around the periphery of the substrate attachment portion 122 for providing fluid communication with the interior of the securement layer 18. While the lower housing 114 and upper housing 118 are illustrated as having a circularly-shaped form annularly relative to the suction housing 110, the lower housing 114 and upper housing 118 may be formed to have other shapes or configurations.

Figure 11:
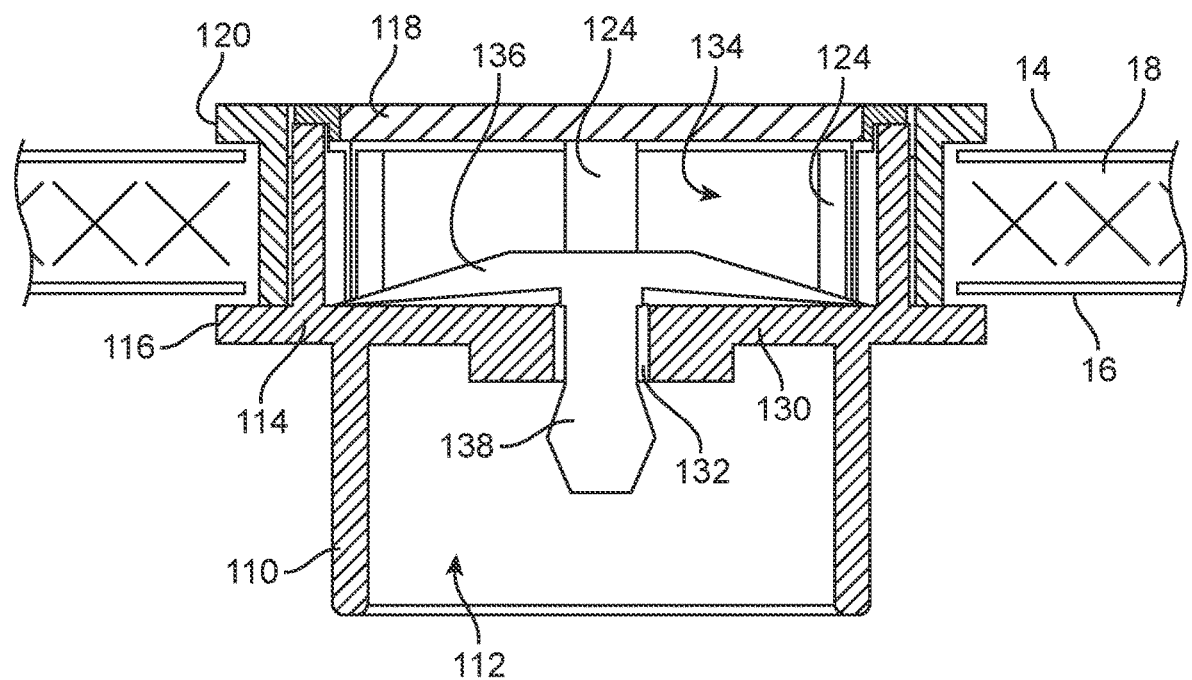
FIG. 11 shows a cross-sectional side view of the suction mechanism of FIGS. 10A and 10B.

FIG. 11 illustrates a cross-sectional side view of a suction assembly attached to a substrate. As shown, the first layer 14 may be attached about the upper shoulder 120 forming a fluid-tight seal and the second layer 16 may be attached about the lower shoulder 116 also forming a fluid-tight seal while the one or more fluid channels 124 defined about the periphery of the substrate attachment portion 122 remain in fluid communication with the interior of the securement layer 18. A housing chamber 134 may be formed between a floor 130 of the lower housing 114 and the upper housing 118 with a valve 136, e.g., umbrella valve, which may be biased towards the floor 130 to maintain the valve 136 in a closed configuration against the floor 130. A retaining member 138 projecting from the valve 136 may extend through an opening 132 defined through the floor 130 and partially into the suction chamber 112. The retaining member 138 may be configured to include a widened, retaining portion which allows for the valve 136 to move between an open and closed configuration until the widened portion abuts against the opening 132 to limit the amount that the valve 136 may open.

During use when the vacuum force is applied to the substrate, the air or gas within the securement layer 18 and also within the housing chamber 134 may evacuate urging the valve 136 into an open configuration where the valve 136 extends into the interior of the housing chamber 134 while limited in travel by the widened, retaining portion of the retaining member 138. With the valve 136 thus opened, the air or gas within the suction chamber 112 may also evacuate via one or more openings defined through the floor 130 and into and through the housing chamber 134 and out through one or more fluid channels 124 causing the suction housing 110 to adhere to the underlying contacted tissue surface due to the negative pressure created within the suction chamber 112. As the valve 136 may be optionally biased to close against the floor 130, once the suction pressure has reached an equilibrium between the housing chamber 134 and suction chamber 112 (or when the suction pressure has dropped below the biased closing force of the valve 136), the valve 136 may close against the floor 130 to seal the suction chamber 112 from the housing chamber 134. In this manner, the suction securement between the suction housing 110 and the adhered tissue surface may be maintained individually between each of the suction assemblies 22 and tissue surface. This may be especially helpful in the event that vacuum pressure is lost within the securement layer 18 during a procedure as each of the individual suction assemblies 22 may maintain suction adherence to the tissue surface independently of one another.

Figure 12A:
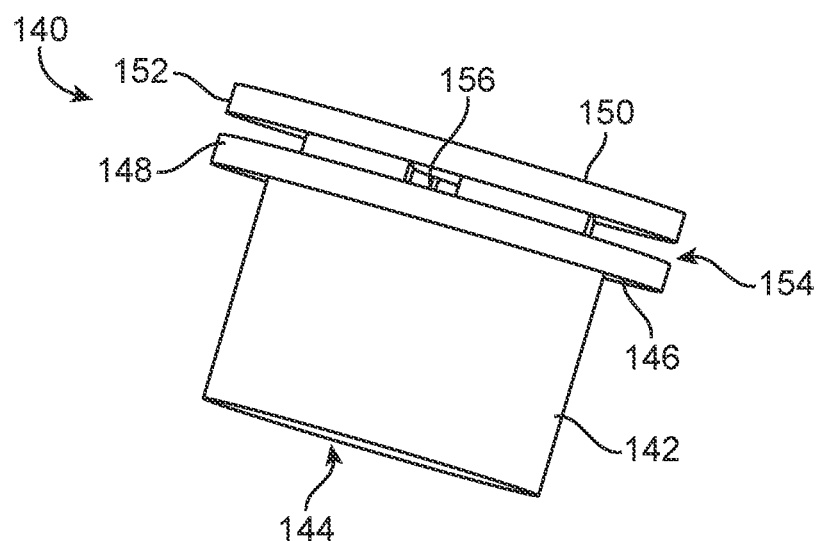
FIGS. 12A and 12B show various perspective views of another variation of an individual suction mechanism for temporary adherence to a tissue region.
Figure 12B:
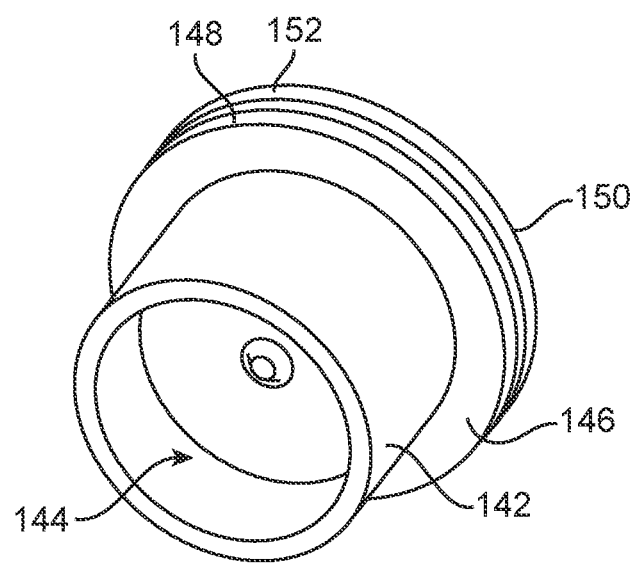

Another variation of the suction assembly 140 is shown in the various perspective views of FIGS. 12A and 12B which illustrate a suction housing 142 defining a suction chamber 144 similarly formed from a lower housing 146 having a lower shoulder 148. An upper housing 150 having an upper shoulder 152 may attach to the lower housing 146 and form a substrate attachment portion 154 about a periphery of the housing assembly. Also, one or more fluid channels 156 may be defined about the periphery of the substrate attachment portion 154.

Figure 13:
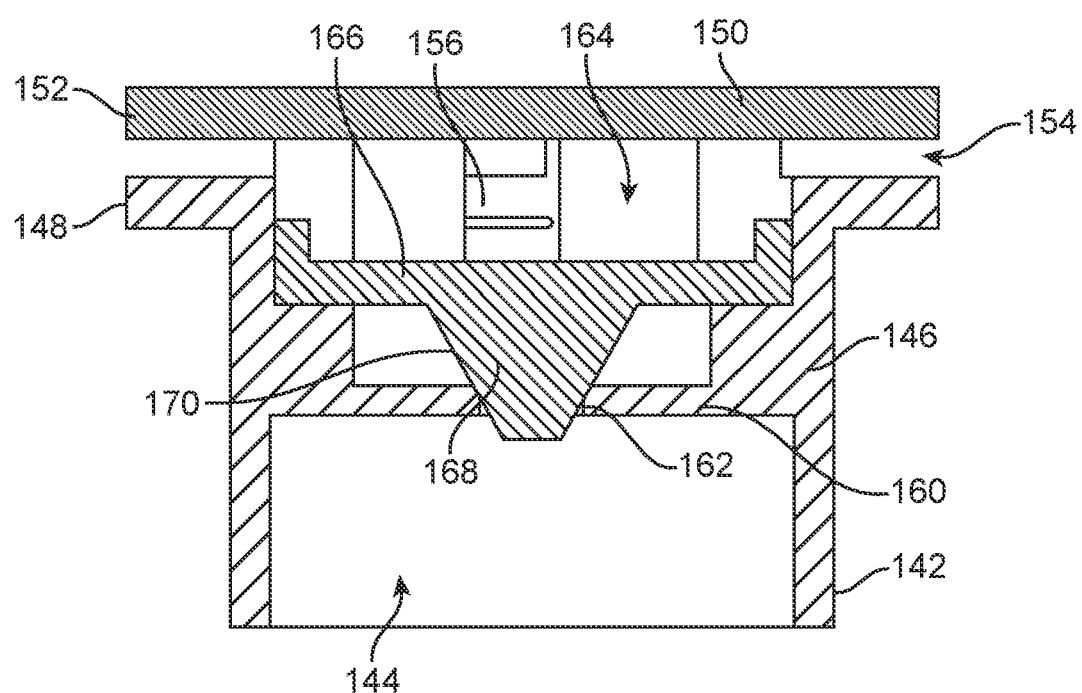
FIG. 13 shows a cross-sectional side view of the suction mechanism of FIGS. 12A and 12B.

As shown in the cross-sectional side view of FIG. 13, the manner in which the valve 166 is designed and positioned within the housing chamber 164 may allow for the height between the lower shoulder 148 and upper shoulder 152 to be reduced relative to previous embodiments while still allowing for fluid communication through the one or more fluid channels 156 with the securement layer 18. This reduced height may also allow for a substrate which is relatively thinner. The valve 166 may be biased to remain in a closed configured where an outer sealing surface 170 of sealing member 168 is urged against an opening 162 defined over the floor 160 of the lower housing 146. The sealing member 168 may be configured in a conical shape projecting from the valve body such that when the vacuum is applied to the substrate, the valve 166 may be urged into its open configuration such that the sealing surface 170 is lifted away from the opening 162 allowing for the negative pressure within the suction chamber 144 to adhere the underlying tissue surface to the suction housing 142. As described above, when the suction pressure has reached an equilibrium between the housing chamber 164 and suction chamber 144 (or when the suction pressure has dropped below the biased closing force of the valve 166), the valve 166 may close against the floor 160 to seal the suction chamber 144 from the housing chamber 164. This allows for the individual suction assembly to adhere to the tissue surface.

Figure 14:
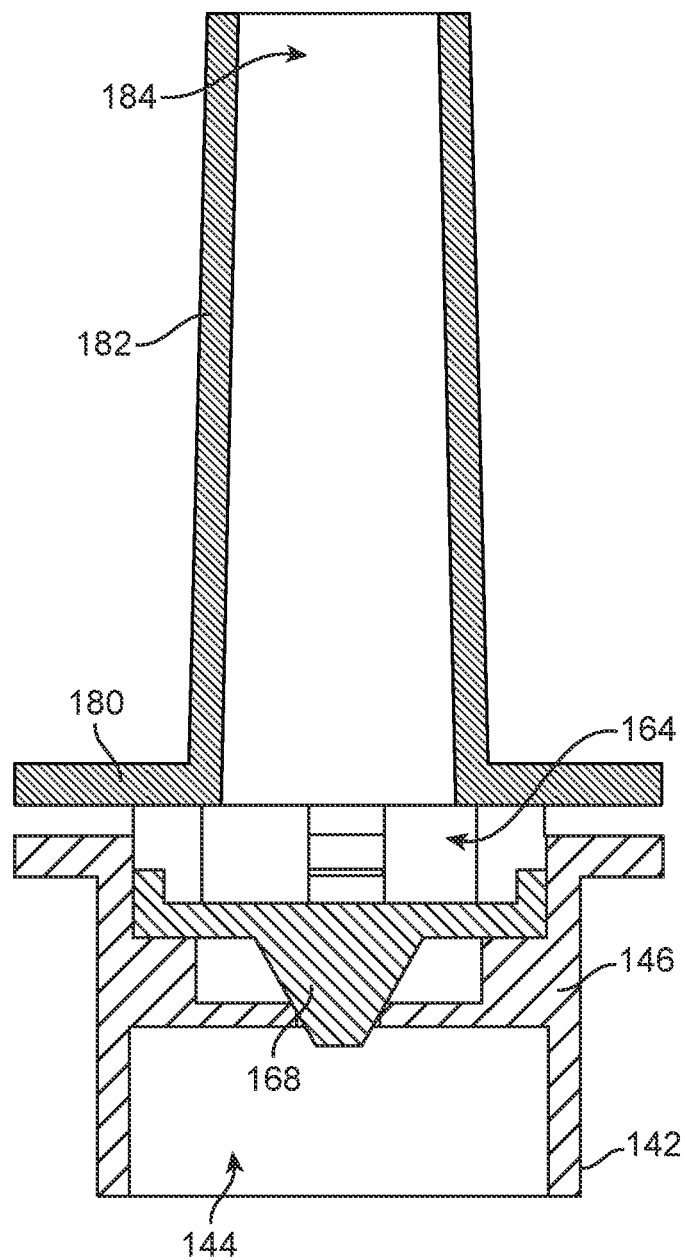
FIG. 14 shows a cross-sectional side view of another variation of an individual suction mechanism.

As previously described, the vacuum tube attachment may be coupled to the substrate for providing fluid communication between a pump and the securement layer of the substrate and suction assemblies. While the vacuum tube attachment may be coupled at any location over the substrate, the attachment may also be coupled to one of the suction assemblies. FIG. 14 shows a cross-sectional side view of one variation where a vacuum tube 182 having a lumen 184 defined through the length of the tube 182 may be attached directly to at least one of the suction assemblies. A distal end of the tube 182 may be attached to the housing of the suction assembly such that the lumen 184 may be fluidly coupled directly to the housing chamber 164. A proximal end of the tube 182 may be fluidly attached to a fluid line for communication with a pump such that when the pump is actuated, the vacuum force may be applied through the lumen 184 and the attached suction assembly. As the suction assembly is fluidly coupled with the securement layer and the other suction assemblies, the vacuum force may applied to the entire substrate and suction assemblies accordingly.

Turning now to other uses or implementations of the positioning platform 10, various laparoscopic procedures may be facilitated using any of the platform embodiments described herein. One particular procedure may involve the use of the platform for establishing a pneumoperitoneal cavity in a patient via insufflation in preparation for an abdominal (or other cavity) procedure. The practitioner typically identifies a location along the patient body, such as the abdomen, where an instrument such as a Veress needle may be penetrated through the skin until the tip reaches just inside the peritoneum. The practitioner oftentimes inserts the needle blindly into the patient body which may result in an unintended injury. For instance, if a portion of the bowel is adhered to the inner wall of the peritoneum, the needle may be inserted over the adhesion resulting in the bowel being pierced or nicked.

Once the needle has been suitably positioned within the patient body, the cavity is then inflated through the needle and a primary trocar may be inserted, also blindly, into the peritoneum. For patients with adhesions, a similar complication as with the needle insertion can occur with the trocar. Another instrument such as a laparopscopic camera may then be inserted into the peritoneum through the primary trocar, for instance, to facilitate the insertion of additional trocars into the patient under direct vision to reduce the risk of internal damage.

With the positioning platform 10 adhered to the skin surface S, the platform 10 may be used to lift the region of tissue of tissue where the needle and/or trocar will be inserted to facilitate the separation of any bowel tissue from the interior of the abdominal wall. Lifting of the tissue area may also help the practitioner to assess for the existence of any adhesions prior to the insertion of the needle and/or trocar.

Figure 15:
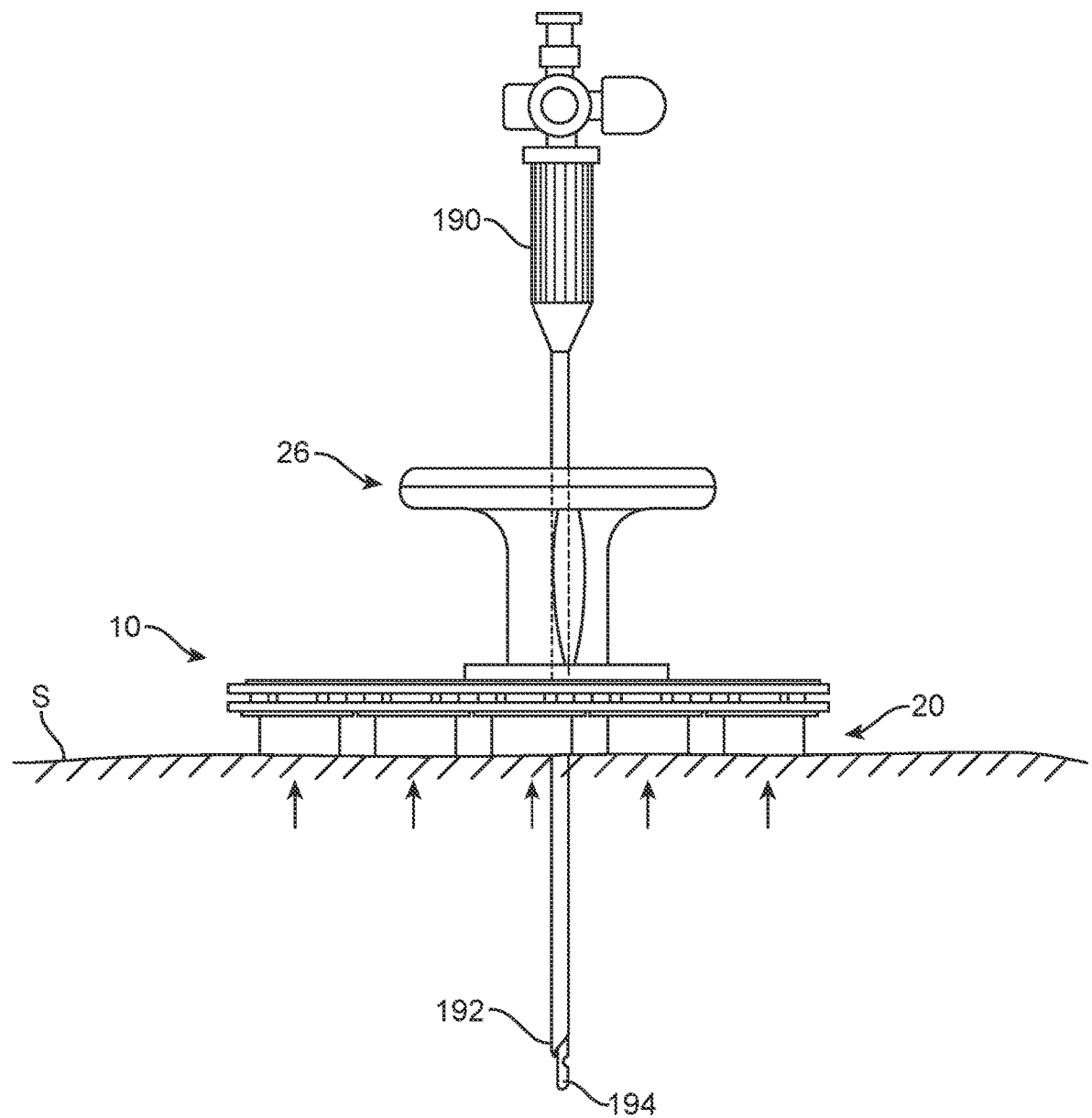
FIG. 15 shows a side view of the platform used in combination with a needle.

An example is shown in the side view of FIG. 15 which illustrates the application of the platform 10 against the skin surface S which may be lifted away from the patient in order to lift the adhered tissue and provide feedback as to the presence of any adhesions. Once the assessment has been made, the needle 190 may be inserted through positioning guide 26 until the piercing tip 192 of the needle or blunt tip 194 has been inserted past the interior tissue wall away from adhesions. Alternatively, the platform 10 may be removed from the tissue region once the assessment has been completed with the platform 10 and the needle 190 may be inserted directly into and through the skin surface S.

Figure 16:
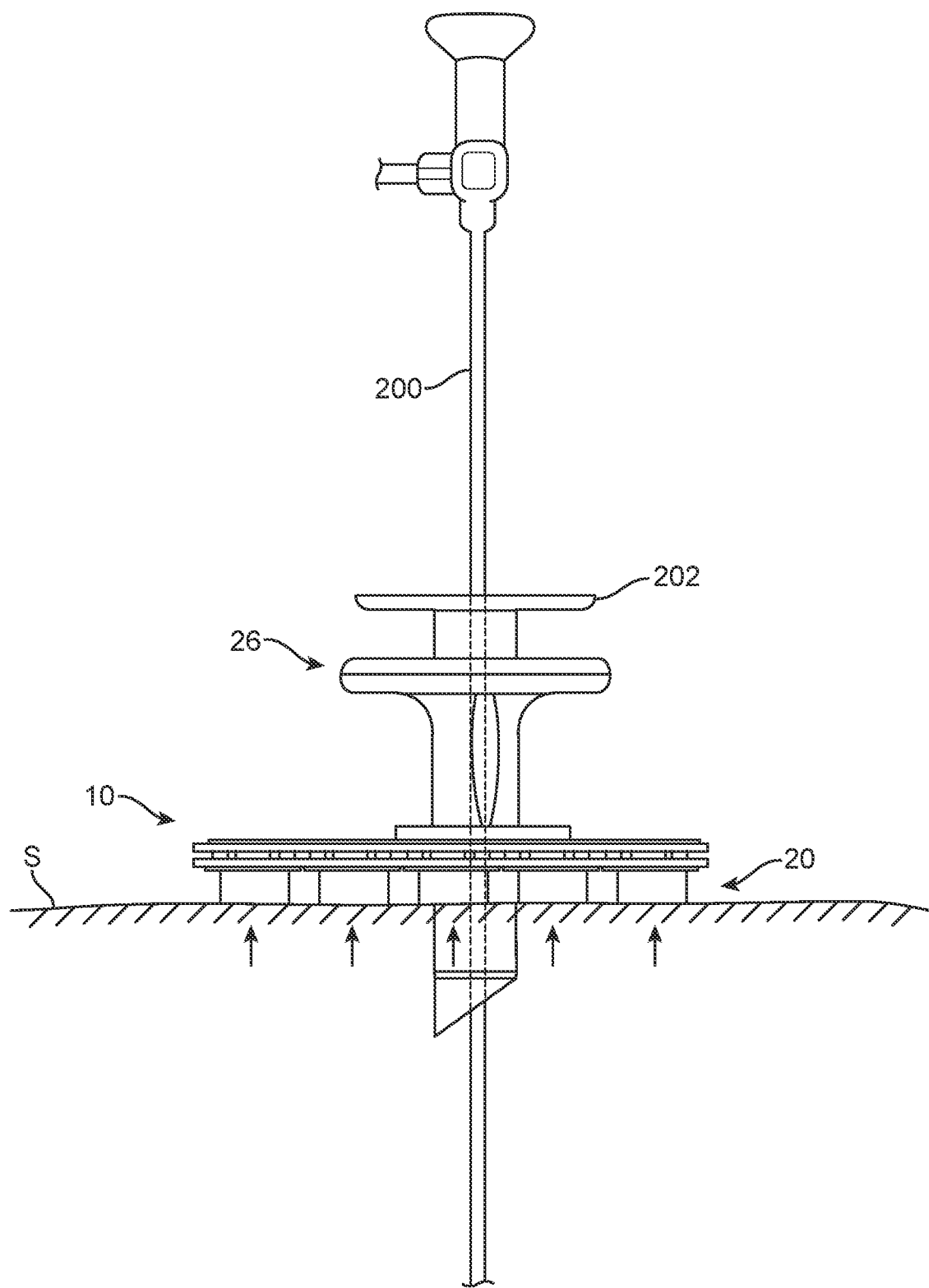
FIG. 16 shows a side view of the platform used in combination with an imaging instrument such as a laparoscope.

In other variations, the platform 10 may be utilized directly with an imaging instrument such as a laparoscope 200, as shown in the side view of FIG. 16. After trocar insertion through the skin surface S, the trocar may be removed leaving the cannula sleeve 202 in place through the tissue region. The laparoscope 200 may be inserted, e.g., directly through the cannula sleeve 202 in order to provide for direct visualization within the body cavity.

Figure 17:
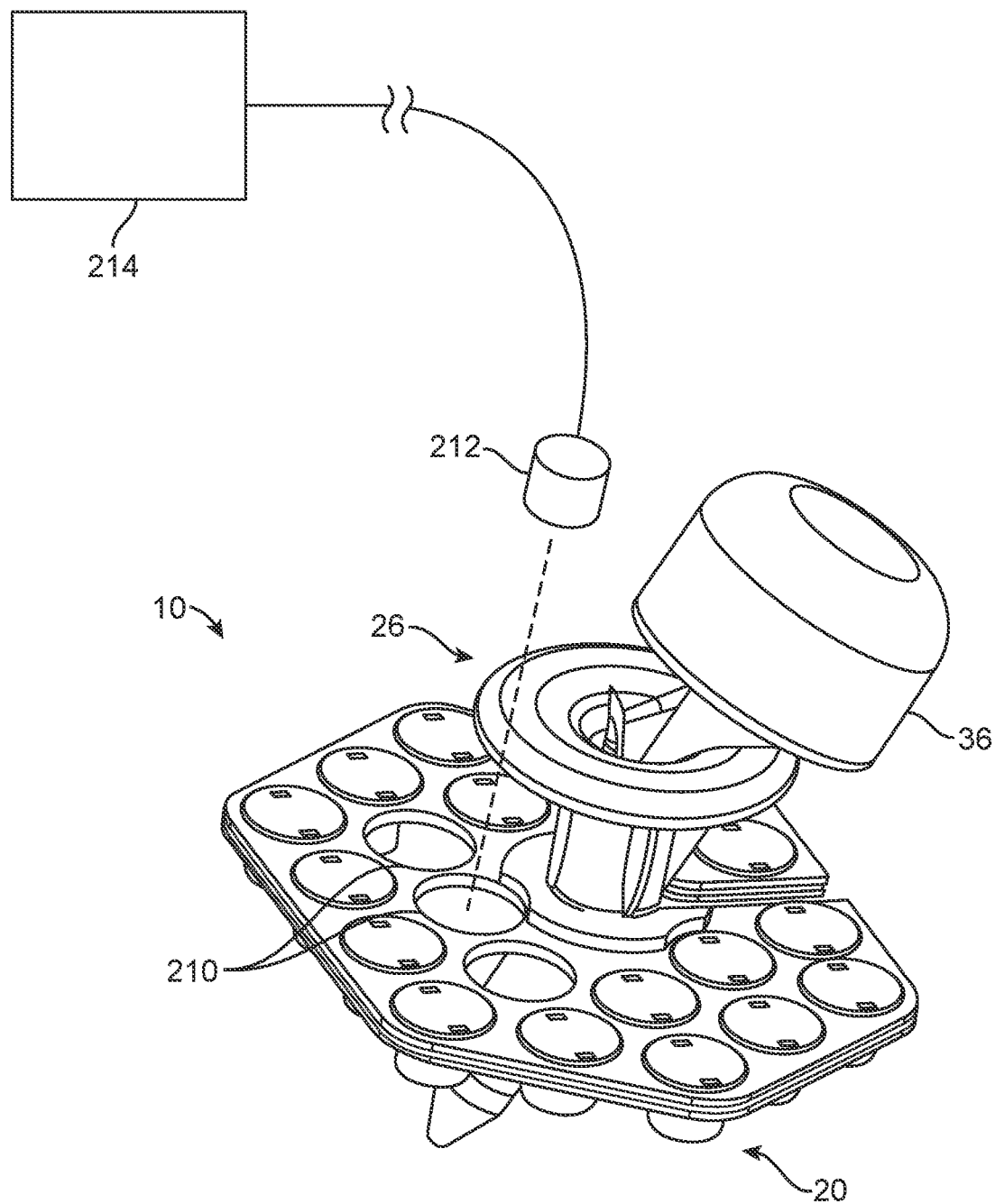
FIG. 17 shows a perspective view of the platform having an integrated ultrasound transducer to provide imaging while in use with the platform.

In yet another variation, the platform 10 may be used in combination with an imaging instrument such as an ultrasound transducer 212 which may be in communication with either a controller 47 (as previously described) or a separate ultrasound controller 214, as shown in the perspective view of FIG. 17. The ultrasound transducer 212 may be used to determine, e.g., whether any adhesions are present underlying the skin surface prior to the application of the platform 10 against the tissue surface. The ultrasound transducer 212 may be initially applied to the skin and then removed to allow for the use of the platform 10 but in other variations, the ultrasound transducer 212 may be incorporated directly with the platform 10. One variation is shown where one or more openings 210 may be formed through the platform 10 next to positioning guide 26 where an ultrasound transducer 212 may be integrated with the platform 10 at one of the openings 210. The transducer 212 may be used to provide for real time imaging of the tissue region directly below the platform 10 prior to and during trocar insertion while the platform 10 is adhered directly to the skin surface S.

When the trocar is removed, gas from the pneumoperitoneum can be evacuated through the opening or may leak through the opening. In order to maintain a fluid-tight seal through the opening in the tissue or through the trocar to maintain the pneumoperitoneum, a seal or stopper may be inserted to cover the trocar opening or directly over the tissue opening. At the end of the procedure, openings (e.g., larger than 12 mm) through the abdominal wall may be sutured closed.

The applications of the disclosed invention discussed above are not limited to certain treatments or regions of the body but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of positioning an instrument, comprising:
   positioning a second surface of a substrate in proximity to a tissue surface, where the second surface is opposite to a first surface of the substrate;
   adhering the second surface to a tissue surface, wherein an interior of the substrate is in fluid communication through an opening defined in the substrate, and wherein adhering the second surface further comprises collapsing the first surface and the second surface against a securement layer positioned therebetween by applying a vacuum force through the opening such that movement of the first surface against the second surface is inhibited;

advancing an instrument through or along an instrument positioning guide projecting from the first surface of the substrate and into the tissue surface; and applying a counterforce to the substrate while advancing the instrument into the tissue surface.

2. The method of claim 1 wherein adhering the second surface comprises adhering the second surface to the tissue surface via one or more suction assemblies in fluid communication with the interior of the substrate.

3. The method of claim 1 wherein advancing the instrument comprises advancing a needle through or along the instrument positioning guide.

4. The method of claim 3 further comprising adjusting an angle of the needle relative to the substrate.

5. The method of claim 1 wherein applying the counterforce comprises applying the counterforce to the instrument positioning guide while advancing the instrument into the tissue surface.

6. The method of claim 1 further comprising retracting the tissue surface via the substrate.

7. The method of claim 1 further comprising detecting for features within a region of tissue via an ultrasound transducer integrated along the substrate prior to advancing the instrument.

8. A method of positioning an instrument, comprising:

positioning a second surface of a substrate in proximity to a tissue surface, where the second surface is opposite to a first surface of the substrate;

adhering the second surface to a tissue surface, wherein adhering the second surface further comprises collapsing the first surface and the second surface against a securement layer positioned therebetween such that movement of the first surface against the second surface is inhibited when a vacuum force is applied through an opening defined in the substrate;

reconfiguring a shape of the substrate while adhering the tissue surface such that the tissue surface is reconfigured accordingly by applying a vacuum force through the opening defined in the substrate, wherein the opening is in fluid communication with an interior of the substrate;

advancing an instrument through or along an instrument positioning guide projecting from the first surface of the substrate and into the tissue surface; and applying a counterforce to the substrate while advancing the instrument into the tissue surface.

9. The method of claim 8 wherein adhering the second surface comprises adhering the second surface to the tissue surface via one or more suction assemblies in fluid communication with the interior of the substrate.

10. The method of claim 8 wherein advancing the instrument comprises advancing a needle through or along the instrument positioning guide.

11. The method of claim 10 further comprising adjusting an angle of the needle relative to the substrate.

12. The method of claim 8 wherein applying the counterforce comprises applying the counterforce to the instrument positioning guide while advancing the instrument into the tissue surface.

13. The method of claim 8 further comprising retracting the tissue surface via the substrate.

14. The method of claim 8 further comprising detecting for features within a region of tissue via an ultrasound transducer integrated along the substrate prior to advancing the instrument.

* * * * *